US006350604B1

(12) United States Patent
Hirayama et al.

(10) Patent No.: US 6,350,604 B1
(45) Date of Patent: Feb. 26, 2002

(54) ALKALINE LIPOLYTIC ENZYME

(75) Inventors: Satoshi Hirayama; Rikako Taira, both of Chiba (JP); Kim Borch, København K (DK); Thomas Sandal, Herlev (DK); Torben Halkier, Birkerød (DK); Karen Margrethe Oxenbøll, Charlottenlund (DK); Bjarne Rønfeldt Nielsen, Virum (DK)

(73) Assignee: Novozymes A/S, Bagsuaerd (DK)

( * ) Notice: Subject to any disclaimer, the term of this patent is extended or adjusted under 35 U.S.C. 154(b) by 0 days.

(21) Appl. No.: 09/177,234

(22) Filed: Oct. 22, 1998

Related U.S. Application Data

(63) Continuation of application No. PCT/DK97/00179, filed on Apr. 22, 1997.

(30) Foreign Application Priority Data

Apr. 25, 1996 (DK) .............................. 500/96
Apr. 25, 1996 (DK) .............................. 501/96

(51) Int. Cl.$^7$ .................... C12N 9/20; C12N 9/12; C12N 1/20; C12N 15/00; C07H 21/04
(52) U.S. Cl. .............. 435/198; 435/195; 435/252.3; 435/320.1; 536/23.2; 536/23.74; 530/350; 510/226
(58) Field of Search ................ 435/195, 198, 435/252.3, 320.1; 536/23.2, 23.74; 530/350; 510/226

(56) References Cited

U.S. PATENT DOCUMENTS 4,511,655 A   4/1985   Minai et al. ............... 435/149
4,985,365 A   1/1991   Mitsuda et al. ............ 435/280

FOREIGN PATENT DOCUMENTS

| EP | 0 218 272 A1 | 4/1987 |
| JP | 61 289884 | 12/1986 |
| WO | WO 94/14940 | 7/1994 |
| WO | WO 94/14964 | 7/1994 |
| WO | WO 96/13578 | 5/1996 |

OTHER PUBLICATIONS

Van Tilburg et al. (1993) Applied And Environmental Microbiology 59(1):236–242.

Leger et al. (1986) J. of Invertebrate Pathology 48:85–95.

Jackson et al. (1985) Ann. Appl. Biol. 106:39–48.

Rapp et al. (1992) Enzyme Microb. Technol. 14:938–943.

Roberts et al. (1987) Mycologia 79(2):265–273.

Soliday et al. (1984) Proc. Natl. Acad. Sci., U.S.A. 81:3939–3943.

Kunert et al. (1987) Biológia 42(3):285–293.

*Primary Examiner*—Ponnathapu Achutamurthy
*Assistant Examiner*—Tekchand Saidha
(74) *Attorney, Agent, or Firm*—Elias J. Lambiris; Jason I. Garbell

(57) ABSTRACT

Lipolytic enzymes with high activity at alkaline pH in the absence of $Ca^{++}$ can be obtained from filamentous fungi of the genera Gliocladium, Verticillium and Trichophaea and that the lipolytic enzymes are effective for improving the effect of detergents. The lipolytic enzymes have a good washing performance, as expressed by the hydrolysis of oil on textile swatches. The amino acid sequences of the lipolytic enzymes are highly homologous.

13 Claims, 8 Drawing Sheets

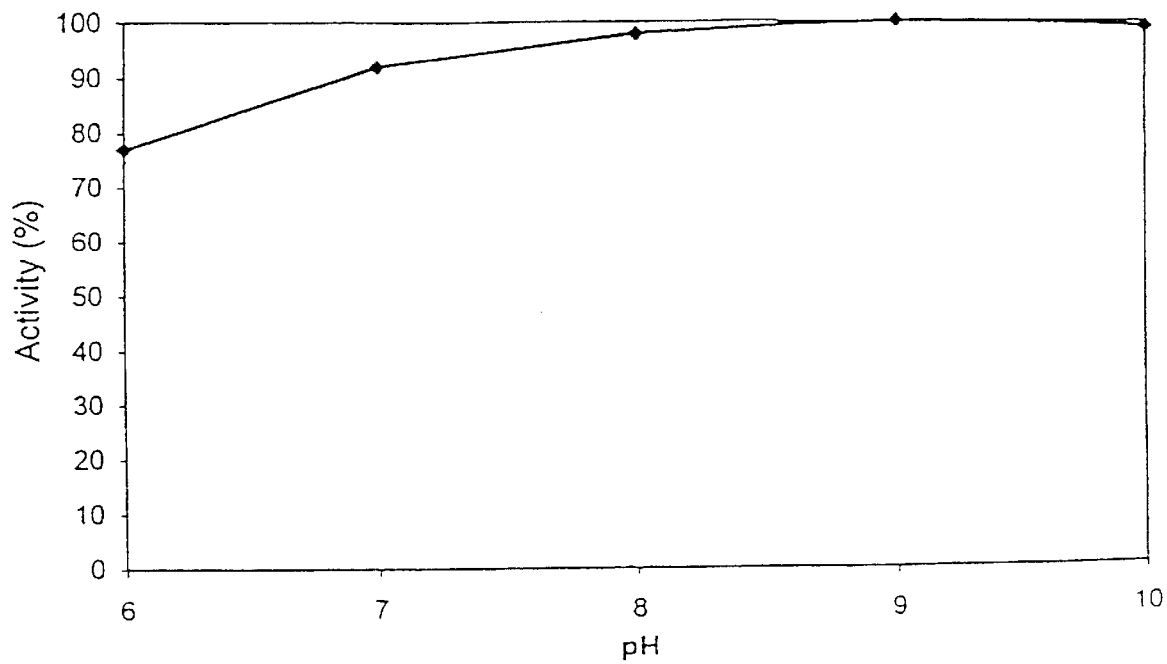
FIG. 6: Verticillium sp. CBS 830.95

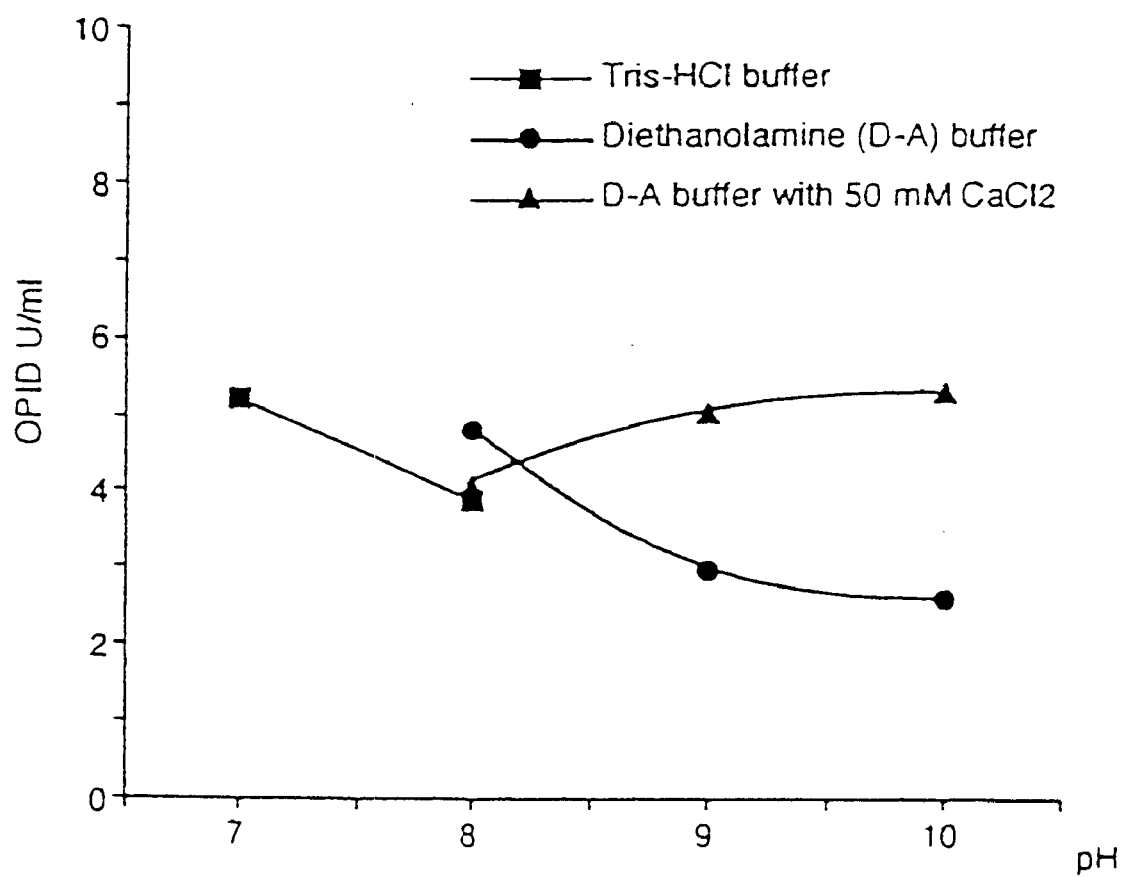
FIG. 7: T. saccata CBS 804.70

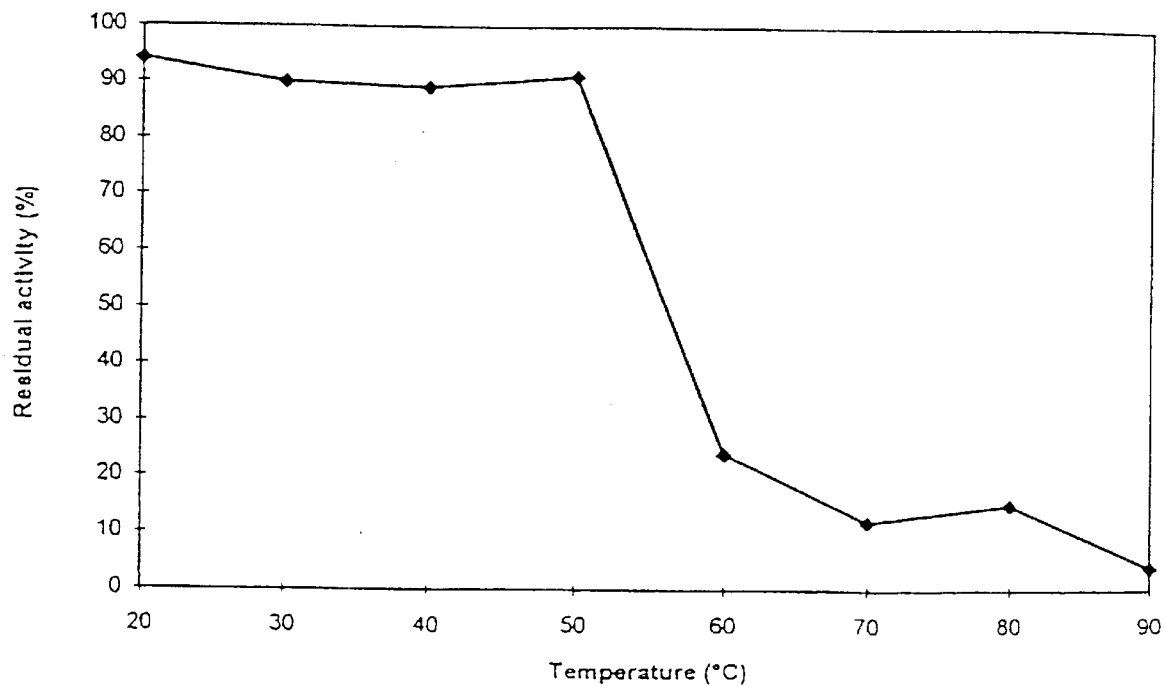
FIG. 8: Verticillium sp. CBS 830.95

SEQUENCE LISTING

<160> NUMBER OF SEQ ID NOS: 8

<210> SEQ ID NO 1
<211> LENGTH: 35
<212> TYPE: PRT
<213> ORGANISM: G. solani

<400> SEQUENCE: 1

Glu Asp Ser Ile Gly Ile Ser Ser Val Leu Val Arg Asp Glu Leu Arg
1               5                   10                  15

Asn Gly Gly Gly Ala Cys Pro Lys Ala Ile Leu Ile Phe Ala Arg Gly
            20                  25                  30

Thr Met Glu
        35

<210> SEQ ID NO 2
<211> LENGTH: 914
<212> TYPE: DNA
<213> ORGANISM: Gliocladium sp.
<220> FEATURE:
<221> NAME/KEY: CDS
<222> LOCATION: (21)...(713)
<221> NAME/KEY: mat_peptide
<222> LOCATION: (114)...(713)
<221> NAME/KEY: sig_peptide
<222> LOCATION: (21)...(113)

<400> SEQUENCE: 2

| | | |
|---|---|---:|
| tgatttttca actctgcatc atg aag ttc ctc tac gtc gtc cag acc ttg atc<br>                                         Met Lys Phe Leu Tyr Val Val Gln Thr Leu Ile<br>                                                  -30                   -25 | | 53 |

```
tgatttttca actctgcatc atg aag ttc ctc tac gtc gtc cag acc ttg atc          53
                     Met Lys Phe Leu Tyr Val Val Gln Thr Leu Ile
                      -30                 -25 gcc ctc gcc ttg gct agg cca ttg cct gag acg gct gtg gaa gtt gac           101
Ala Leu Ala Leu Ala Arg Pro Leu Pro Glu Thr Ala Val Glu Val Asp
-20             -15                 -10                  -5 ctg cag aac cga gaa gat tct atc ggc ata tcc tct gtc ctt gtg cgt          149
Leu Gln Asn Arg Glu Asp Ser Ile Gly Ile Ser Ser Val Leu Val Arg
                 1               5                  10 gac gag ctg cgc aat ggc ggc agc gcg tgc ccc aag gcc att ctc atc          197
Asp Glu Leu Arg Asn Gly Gly Ser Ala Cys Pro Lys Ala Ile Leu Ile
            15                  20                  25 ttt gct cga ggc aca atg gag ctg gat aac atg ggc tta ttg gtc ggg          245
Phe Ala Arg Gly Thr Met Glu Leu Asp Asn Met Gly Leu Leu Val Gly
        30                  35                  40 cca gct ctt gca ggt ggc tta gag ggc atc ttg ggt tcg aac aac ctc          293
Pro Ala Leu Ala Gly Gly Leu Glu Gly Ile Leu Gly Ser Asn Asn Leu
45                  50                  55                  60 tgg gtt caa ggg gtg ggt ggc caa tat gcc gcc aac ctt gag ggc aat          341
Trp Val Gln Gly Val Gly Gly Gln Tyr Ala Ala Asn Leu Glu Gly Asn
                65                  70                  75 cta ttt cca gat gga aca cct cct aaa gcc atc cag gag atg ctt agc          389
Leu Phe Pro Asp Gly Thr Pro Pro Lys Ala Ile Gln Glu Met Leu Ser
            80                  85                  90 ctg ctc caa ttg gcg gac acc aag tgc cca aac tct aag att gtt aca          437
Leu Leu Gln Leu Ala Asp Thr Lys Cys Pro Asn Ser Lys Ile Val Thr
        95                  100                 105 ggg ggt tat agc caa ggt gct gca ctc gtg gcc gct gct att cgc gat          485
Gly Gly Tyr Ser Gln Gly Ala Ala Leu Val Ala Ala Ala Ile Arg Asp
    110                 115                 120 gtc aag gct tcc att cga caa aag att gtg gga acc gta ctc ttt ggg          533
Val Lys Ala Ser Ile Arg Gln Lys Ile Val Gly Thr Val Leu Phe Gly
125                 130                 135                 140 tat act aaa aac aaa cag agg aac gga cag gta gaa aac tac tca act          581
Tyr Thr Lys Asn Lys Gln Arg Asn Gly Gln Val Glu Asn Tyr Ser Thr
                145                 150                 155 gat cgg ctc cgg gtt tac tgt aac ctc gga gac ttg att tgt gaa ggg          629
Asp Arg Leu Arg Val Tyr Cys Asn Leu Gly Asp Leu Ile Cys Glu Gly
            160                 165                 170
```

```
acc ttg att gtt cta cca cca cat ctt ctt tat gga gtc cag gct gct      677
Thr Leu Ile Val Leu Pro Pro His Leu Leu Tyr Gly Val Gln Ala Ala
        175                 180                 185 ggt cca gct gcc cag ttc ctc gcc agc aag atc aat taatttttct            723
Gly Pro Ala Ala Gln Phe Leu Ala Ser Lys Ile Asn
    190                 195                 200 tgatcaatgc atggcagaat gctgccatgt actcagatat ggataggaga gatcatatat     783
ggactatata tagtagctct gccgcatctg tcgaaagttt tgatattctt tcgttcgttg     843
ttagggctga cttattcttg agatgaataa aaaaagatct gtataaagag aaaaaaaaaa     903
aaaaaaaaaa a                                                          914

<210> SEQ ID NO 3
<211> LENGTH: 231
<212> TYPE: PRT
<213> ORGANISM: Gliocladium sp.
<220> FEATURE:
<221> NAME/KEY: SIGNAL
<222> LOCATION: (1)...(31)

<400> SEQUENCE: 3

Met Lys Phe Leu Tyr Val Val Gln Thr Leu Ile Ala Leu Ala Leu Ala
-30                 -25                 -20

Arg Pro Leu Pro Glu Thr Ala Val Glu Val Asp Leu Gln Asn Arg Glu
-15                 -10                  -5                   1

Asp Ser Ile Gly Ile Ser Ser Val Leu Val Arg Asp Glu Leu Arg Asn
                  5                  10                  15

Gly Gly Ser Ala Cys Pro Lys Ala Ile Leu Ile Phe Ala Arg Gly Thr
             20                  25                  30

Met Glu Leu Asp Asn Met Gly Leu Leu Val Gly Pro Ala Leu Ala Gly
         35                  40                  45

Gly Leu Glu Gly Ile Leu Gly Ser Asn Asn Leu Trp Val Gln Gly Val
50                  55                  60                  65

Gly Gly Gln Tyr Ala Ala Asn Leu Glu Gly Asn Leu Phe Pro Asp Gly
                 70                  75                  80

Thr Pro Pro Lys Ala Ile Gln Glu Met Leu Ser Leu Leu Gln Leu Ala
             85                  90                  95

Asp Thr Lys Cys Pro Asn Ser Lys Ile Val Thr Gly Gly Tyr Ser Gln
         100                 105                 110

Gly Ala Ala Leu Val Ala Ala Ala Ile Arg Asp Val Lys Ala Ser Ile
     115                 120                 125

Arg Gln Lys Ile Val Gly Thr Val Leu Phe Gly Tyr Thr Lys Asn Lys
130                 135                 140                 145

Gln Arg Asn Gly Gln Val Glu Asn Tyr Ser Thr Asp Arg Leu Arg Val
                 150                 155                 160

Tyr Cys Asn Leu Gly Asp Leu Ile Cys Glu Gly Thr Leu Ile Val Leu
             165                 170                 175

Pro Pro His Leu Leu Tyr Gly Val Gln Ala Ala Gly Pro Ala Ala Gln
         180                 185                 190

Phe Leu Ala Ser Lys Ile Asn
     195                 200

<210> SEQ ID NO 4
<211> LENGTH: 29
<212> TYPE: PRT
<213> ORGANISM: Verticillium sp.
<220> FEATURE:
<223> OTHER INFORMATION: Xaa at position 22 is an undetermined amino
``` acid

<400> SEQUENCE: 4

```
Glu Asp Ser Phe Gly Ile Ser Ser Val Leu Val Arg Asp Glu Leu Ile
  1               5                  10                  15
Asn Gly Gly Gly Ala Xaa Pro Lys Ala Ile Leu Ile Phe
             20                  25
```

<210> SEQ ID NO 5
<211> LENGTH: 869
<212> TYPE: DNA
<213> ORGANISM: Verticillium sp.
<220> FEATURE:
<221> NAME/KEY: CDS
<222> LOCATION: (43)...(738)
<221> NAME/KEY: mat_peptide
<222> LOCATION: (133)...(738)
<221> NAME/KEY: sig_peptide
<222> LOCATION: (43)...(132)

<400> SEQUENCE: 5

| | |
|---|---:|
| ctcaattcgt gaaagtctga gatcaatttt caagtttgca tt atg aag ttc ctt<br>                                                                                                                    Met Lys Phe Leu<br>                                                                                                                   -30 | 54 |

```
tac att ctt cag acc cta gct acc ctt gcg cta gcc act ccc gta cct      102
Tyr Ile Leu Gln Thr Leu Ala Thr Leu Ala Leu Ala Thr Pro Val Pro
   -25                 -20                 -15 gag acg gta cca gag agt gac ctg caa agt cga gaa gat tct ttt ggt      150
Glu Thr Val Pro Glu Ser Asp Leu Gln Ser Arg Glu Asp Ser Phe Gly
-10                  -5                   1               5 ata tct tct gtt ctc gtg cgt gat gaa ttg atc aat ggt ggc ggc gct      198
Ile Ser Ser Val Leu Val Arg Asp Glu Leu Ile Asn Gly Gly Gly Ala
                 10                  15                  20 tgc ccc aag gct atc ctc atc ttt gct cga gga acg ata gaa ctt gat      246
Cys Pro Lys Ala Ile Leu Ile Phe Ala Arg Gly Thr Ile Glu Leu Asp
         25                  30                  35 aac atg ggc tta ttg gtt ggg cca cct ctt gca gac ggt cta tcg ggt      294
Asn Met Gly Leu Leu Val Gly Pro Pro Leu Ala Asp Gly Leu Ser Gly
     40                  45                  50 atc ttg ggt tca aaa aac ctc tgg gtc caa ggc gtg ggt ggc caa tat      342
Ile Leu Gly Ser Lys Asn Leu Trp Val Gln Gly Val Gly Gly Gln Tyr
 55                  60                  65                  70 gct gca agc ttg gag ggt aat ctc ttt ccg gat ggg acc cct cct caa      390
Ala Ala Ser Leu Glu Gly Asn Leu Phe Pro Asp Gly Thr Pro Pro Gln
                 75                  80                  85 gcc atc cag gag atg att aca ttg ctt caa ttg gcg gat act aaa tgt      438
Ala Ile Gln Glu Met Ile Thr Leu Leu Gln Leu Ala Asp Thr Lys Cys
         90                  95                 100 cca aac tcc aag att gtc act ggg gga tat agt caa ggt gct gct ctc      486
Pro Asn Ser Lys Ile Val Thr Gly Gly Tyr Ser Gln Gly Ala Ala Leu
    105                 110                 115 gtg gcc gca gca att cgg gat gtc aag gct tcg atc cga cag aag att      534
Val Ala Ala Ala Ile Arg Asp Val Lys Ala Ser Ile Arg Gln Lys Ile
120                 125                 130 gta gga act gta ctg ttc ggg tac tcc aaa aac aaa cag agg aac ggt      582
Val Gly Thr Val Leu Phe Gly Tyr Ser Lys Asn Lys Gln Arg Asn Gly
135                 140                 145                 150 cag gta gaa aac tac tct aat gac cga ctc cga gtt tat tgc aac cct      630
Gln Val Glu Asn Tyr Ser Asn Asp Arg Leu Arg Val Tyr Cys Asn Pro
                155                 160                 165 ggg gat tta att tgc gag ggg acc ttg att gtt ctg cca gtg cac ctc      678
Gly Asp Leu Ile Cys Glu Gly Thr Leu Ile Val Leu Pro Val His Leu
```

-continued

```
                  170                 175                 180
ctt tat gga aac caa gct tct ggt cct gca gca caa ttc ctc gct agt      726
Leu Tyr Gly Asn Gln Ala Ser Gly Pro Ala Ala Gln Phe Leu Ala Ser
            185                 190                 195 aag atc aat tct tagttgaatt gtagccaacc ggatatggct ggggatgggc          778
Lys Ile Asn Ser
    200 ccaatcgtaa cctatataat aggcttcatg ccatgtctta ttgctaatat acgaaagaa     838 attctgaata cataaaaaaa aaaaaaaaaa a                                   869
```

<210> SEQ ID NO 6
<211> LENGTH: 232
<212> TYPE: PRT
<213> ORGANISM: Verticillium sp.
<220> FEATURE:
<221> NAME/KEY: SIGNAL
<222> LOCATION: (1)...(30)

<400> SEQUENCE: 6

```
Met Lys Phe Leu Tyr Ile Leu Gln Thr Leu Ala Thr Leu Ala Leu Ala
-30                 -25                 -20                 -15

Thr Pro Val Pro Glu Thr Val Pro Glu Ser Asp Leu Gln Ser Arg Glu
            -10                  -5                   1

Asp Ser Phe Gly Ile Ser Ser Val Leu Val Arg Asp Glu Leu Ile Asn
         5                  10                  15

Gly Gly Gly Ala Cys Pro Lys Ala Ile Leu Ile Phe Ala Arg Gly Thr
        20                  25                  30

Ile Glu Leu Asp Asn Met Gly Leu Leu Val Gly Pro Pro Leu Ala Asp
35                  40                  45                  50

Gly Leu Ser Gly Ile Leu Gly Ser Lys Asn Leu Trp Val Gln Gly Val
                55                  60                  65

Gly Gly Gln Tyr Ala Ala Ser Leu Glu Gly Asn Leu Phe Pro Asp Gly
            70                  75                  80

Thr Pro Pro Gln Ala Ile Gln Glu Met Ile Thr Leu Leu Gln Leu Ala
        85                  90                  95

Asp Thr Lys Cys Pro Asn Ser Lys Ile Val Thr Gly Gly Tyr Ser Gln
    100                 105                 110

Gly Ala Ala Leu Val Ala Ala Ala Ile Arg Asp Val Lys Ala Ser Ile
115                 120                 125                 130

Arg Gln Lys Ile Val Gly Thr Val Leu Phe Gly Tyr Ser Lys Asn Lys
                135                 140                 145

Gln Arg Asn Gly Gln Val Glu Asn Tyr Ser Asn Asp Arg Leu Arg Val
            150                 155                 160

Tyr Cys Asn Pro Gly Asp Leu Ile Cys Glu Gly Thr Leu Ile Val Leu
        165                 170                 175

Pro Val His Leu Leu Tyr Gly Asn Gln Ala Ser Gly Pro Ala Ala Gln
    180                 185                 190

Phe Leu Ala Ser Lys Ile Asn Ser
195                 200
```

<210> SEQ ID NO 7
<211> LENGTH: 999
<212> TYPE: DNA
<213> ORGANISM: Trichophaea saccata
<220> FEATURE:
<221> NAME/KEY: CDS
<222> LOCATION: (68)...(763)
<221> NAME/KEY: mat_peptide -continued

```
<222> LOCATION: (161)...(763)
<221> NAME/KEY: sig_peptide
<222> LOCATION: (68)...(160)

<400> SEQUENCE: 7
cttggtaccg agctcggatc cgaattcgca caacgggttt ccgacttttg atttccaacg      60 ctgcatc atg aag ttc ctc tac gcc gtc cag acc tta atc gcc ttt gca      109
        Met Lys Phe Leu Tyr Ala Val Gln Thr Leu Ile Ala Phe Ala
         -30             -25                 -20 ctg gct acg cca gtg ccc gag acg gct gta gca gtt gat ctg cag aat      157
Leu Ala Thr Pro Val Pro Glu Thr Ala Val Ala Val Asp Leu Gln Asn
        -15                 -10                 -5 cga gaa gat tct atc ggc ata tcc tct gtc ctt gtg cgt gat gaa ctg      205
Arg Glu Asp Ser Ile Gly Ile Ser Ser Val Leu Val Arg Asp Glu Leu
 1               5                   10                  15 cgc aat ggc ggc ggc gcg tgt ccc aag gcc att ctc atc ttt gct aga      253
Arg Asn Gly Gly Gly Ala Cys Pro Lys Ala Ile Leu Ile Phe Ala Arg
             20                  25                  30 ggt aca atg gag ctg gat aac atg ggc tta tta gtc ggg cca gct ctt      301
Gly Thr Met Glu Leu Asp Asn Met Gly Leu Leu Val Gly Pro Ala Leu
         35                  40                  45 gca ggt ggc tta gag gct atg ctg ggt tca aat aac ctc tgg gtc caa      349
Ala Gly Gly Leu Glu Ala Met Leu Gly Ser Asn Asn Leu Trp Val Gln
     50                  55                  60 ggt gta ggt ggc caa tat gct gcc aat ctc gag ggc aat cta ttt cca      397
Gly Val Gly Gly Gln Tyr Ala Ala Asn Leu Glu Gly Asn Leu Phe Pro
 65                  70                  75 gat gga aca cct ccc aaa gcc atc cag gag atg ctt agt ctg ctc caa      445
Asp Gly Thr Pro Pro Lys Ala Ile Gln Glu Met Leu Ser Leu Leu Gln
 80                  85                  90                  95 tta gcg gac acc aag tgt cca aac tct aag att gtc aca ggg ggg tat      493
Leu Ala Asp Thr Lys Cys Pro Asn Ser Lys Ile Val Thr Gly Gly Tyr
                100                 105                 110 agc caa ggc gct gca ctc gta gcc gct gct att cgc gac gtc aag gct      541
Ser Gln Gly Ala Ala Leu Val Ala Ala Ala Ile Arg Asp Val Lys Ala
             115                 120                 125 tcc att cga caa aag att gta gga act gta ctc ttt ggg tac acc aaa      589
Ser Ile Arg Gln Lys Ile Val Gly Thr Val Leu Phe Gly Tyr Thr Lys
         130                 135                 140 aac aaa cag aag aac gga cag gta gaa aac tac tca act gat cga ctc      637
Asn Lys Gln Lys Asn Gly Gln Val Glu Asn Tyr Ser Thr Asp Arg Leu
 145                 150                 155 cgg gtt tat tgc aac gcc gga gac ttg att tgt caa ggg acc ttg att      685
Arg Val Tyr Cys Asn Ala Gly Asp Leu Ile Cys Gln Gly Thr Leu Ile
 160                 165                 170                 175 gtt ctg cca gcg cat ctt ctt tac gga gat cag gct gct ggt cca gca      733
Val Leu Pro Ala His Leu Leu Tyr Gly Asp Gln Ala Ala Gly Pro Ala
                180                 185                 190 gcc cag ttc ctt gcc agc aag atc agt tca taattgcttg atcaacgcat        783
Ala Gln Phe Leu Ala Ser Lys Ile Ser Ser
             195                 200 cacagattgc tgccatgcac ccatatatgg ataggagaga tcaaatatgg accttacata    843
gtcgctctac cgcatctgct aagaatattt gatattcctt cgttccttct taaggctaat    903
gtatcctcga gatggatgat taagatcagt ataaagagat gtaacaattt atacaggcga    963
tctaggtaga tactaagact acatttaagt gtgaaa                              999

<210> SEQ ID NO 8
<211> LENGTH: 232
```

```
<212> TYPE: PRT
<213> ORGANISM: Trichophaea saccata
<220> FEATURE:
<221> NAME/KEY: SIGNAL
<222> LOCATION: (1)...(31)

<400> SEQUENCE: 8
```

Met Lys Phe Leu Tyr Ala Val Gln Thr Leu Ile Ala Phe Ala Leu Ala
    -30                 -25                 -20

Thr Pro Val Pro Glu Thr Ala Val Ala Val Asp Leu Gln Asn Arg Glu
-15                 -10                  -5                   1

Asp Ser Ile Gly Ile Ser Ser Val Leu Val Arg Asp Glu Leu Arg Asn
            5                   10                  15

Gly Gly Gly Ala Cys Pro Lys Ala Ile Leu Ile Phe Ala Arg Gly Thr
            20                  25                  30

Met Glu Leu Asp Asn Met Gly Leu Leu Val Gly Pro Ala Leu Ala Gly
        35                  40                  45

Gly Leu Glu Ala Met Leu Gly Ser Asn Asn Leu Trp Val Gln Gly Val
50                  55                  60                  65

Gly Gly Gln Tyr Ala Ala Asn Leu Glu Gly Asn Leu Phe Pro Asp Gly
            70                  75                  80

Thr Pro Pro Lys Ala Ile Gln Glu Met Leu Ser Leu Leu Gln Leu Ala
            85                  90                  95

Asp Thr Lys Cys Pro Asn Ser Lys Ile Val Thr Gly Gly Tyr Ser Gln
            100                 105                 110

Gly Ala Ala Leu Val Ala Ala Ala Ile Arg Asp Val Lys Ala Ser Ile
        115                 120                 125

Arg Gln Lys Ile Val Gly Thr Val Leu Phe Gly Tyr Thr Lys Asn Lys
130                 135                 140                 145

Gln Lys Asn Gly Gln Val Glu Asn Tyr Ser Thr Asp Arg Leu Arg Val
            150                 155                 160

Tyr Cys Asn Ala Gly Asp Leu Ile Cys Gln Gly Thr Leu Ile Val Leu
            165                 170                 175

Pro Ala His Leu Leu Tyr Gly Asp Gln Ala Ala Gly Pro Ala Ala Gln
            180                 185                 190

Phe Leu Ala Ser Lys Ile Ser Ser
    195                 200

ALKALINE LIPOLYTIC ENZYME

CROSS-REFERENCE TO RELATED APPLICATION

This application is a continuation of PCT/DK97/00179 filed Apr. 22, 1997 which claims priority under 35 U.S.C. 119 of Danish applications 501/96 filed Apr. 25, 1996 and 500/96 filed Apr. 25, 1996, the contents are fully incorporated herein by reference.

TECHNICAL FIELD

This invention relates to an alkaline lipolytic enzyme, a detergent composition comprising the enzyme, methods of producing the enzyme, an isolated DNA sequence encoding the enzyme, a recombinant expression vector comprising the DNA sequence and cells comprising the DNA sequence or the vector.

BACKGROUND ART

For a number of years lipolytic enzymes have been used as detergent additives to remove lipid or fatty stains.

Thus, the prior art suggests the use of various lipolytic enzymes with lipase or cutinase activity as detergent additives. Examples include microbial lipolytic enzymes derived from strains of Fusarium, e.g. *F. oxysporum* (EP 130 064) and *F. solani f.* sp. *pisi* (WO 90/09446), *Humicola lanuginosa* (also called *Thermomyces lanuginosus*, EP 258 068 and EP 305 216), Pseudomonas, e.g. *P. alcaligenes* and *P. pseudoalcaligenes* (EP 218 272), *P. cepacia* (EP 331 376), *P. mendocina* (WO 88/09367), and Bacillus, e.g. *B. subtilis* (Dartois et al., (1993) Biochemica et Biophysica acta 1131, 253–260), *B. stearothermophilus* (JP 64/74992) and *B. pumilus* (WO 91/16422).

It is the object of this invention to provide lipolytic enzymes having good washing performance and stability in a detergent solution.

STATEMENT OF THE INVENTION

Surprisingly, we have found that alkaline lipolytic enzymes can be obtained from filamentous fungi of the genera Gliocladium, Verticillium and Trichophaea and that the lipolytic enzymes are effective for improving the effect of detergents. The lipolytic enzymes have a good washing performance and stability in a detergent solution.

Full length cDNA sequences each encoding a lipolytic enzyme according to the invention were derived from three strains of Giiocladium sp., Verticillium sp. and *Trichophaea saccata* as donor organisms. The cDNA sequences were cloned into the plasmid pYES 2.0 present in *Escherichia coli.*, and the cloned *E. coli* strains were deposited by the inventors, as shown in the table below. The lipolytic enzyme encoding DNA sequence harbored in the deposited *E. coli* strain is believed to have the sequence shown in the positions and listing indicated below, and the amino acid sequence deduced therefrom is shown in the indicated positions and listing.

The information is summarized below:

| Donor organism | Gliocladium sp. | Verticillium sp. | T. saccata |
|---|---|---|---|
| Donor strain | CBS 173.96 | CBS 830.95 | CBS 804.70 |
| E. coli transformant | DSM 10591 | DSM 10590 | DSM 11298 |
| DNA sequence listing | SEQ ID NO: 2 | SEQ ID NO: 5 | SEQ ID NO: 7 |
| DNA positions | 114–713 | 133–738 | 161–763 |
| Amino acid sequence listing | SEQ ID NO: 3 | SEQ ID NO: 6 | SEQ ID NO: 8 |
| Amino acid positions | 1–200 | 1–202 | 1–201 |

Homologies of the above DNA and amino acid sequences were calculated by methods described later in this specification. The following homologies were found between pairs of sequences, amino acid homology at the upper right corner, and DNA homology at the lower left. (given as DNA homology/amino acid homology):

| | Gliocladium sp. | Verticillium sp. | T. saccata |
|---|---|---|---|
| Gliocladium sp. | 100 | 91 | 96 |
| Verticillium sp. | 83 | 100 | 89 |
| T. saccata | 92 | 83 | 100 |

Accordingly, the invention in its various aspects provides:

1. A lipolytic enzyme which is:
   a) a polypeptide encoded by the lipolytic enzyme encoding part of the DNA sequence cloned into a plasmid present in *Escherichia coli* DSM 10591, DSM 10590 or DSM 11298, or
   b) a polypeptide produced by Gliocladium sp. CBS 173.96, Verticillium sp. CBS 830.95 or *Trichophaea saccata* CBS 804.70, or
   c) a polypeptide having an amino acid sequence as shown in positions 1-200 of SEQ ID NO: 3, positions 1–202 of SEQ ID NO: 6, or positions 1–201 of SEQ ID NO: 8, or
   d) an analogue of the polypeptide defined in (a), (b) or (c) which:
      i) is at least 60% homologous with said polypeptide, or
      ii) is immunologically reactive with an antibody raised against said polypeptide in purified form.
2. An alkaline lipolytic enzyme which is derivable from a strain of Gliocladium and has a lipolytic activity at pH 10 in the absence of Ca$^{++}$ above 20% of the lipolytic activity at pH 10 in the presence of 50 mM Ca$^{++}$.
3. An alkaline lipolytic enzyme which is derivable from a strain of Gliocladium and gives a degree of hydrolysis above 15% on cotton/olive oil swatches in the Activity-in-Detergent (AiD) assay.
4. An alkaline lipolytic enzyme which is derivable from a strain of the genus Verticillium and retains more than 90% activity after 30 minutes incubation at pH 10.2, 40° C. in a solution of 0.300 g/l $C_{14}$–$C_{16}$ alkyl sulfate, 0.650 g/l alcohol ethoxylate ($C_{12}$–$C_{14}$, 6 EO), 1.750 zeolite P, 0.145 g/l $Na_2CO_3$, 0.020 g/l acrylate/maleate copolymer and 0.050 g/l carboxymethyl cellulose.
5. An enzymatic detergent composition comprising a surfactant and the lipolytic enzyme of any preceding claim.
6. A method of producing an alkaline lipolytic enzyme, comprising cultivation of a lipolytic enzyme-producing strain of Gliocladium, Verticillium or Trichophaea in a suitable nutrient medium, followed by recovery of the alkaline lipolytic enzyme.

7. A method for producing an alkaline lipolytic enzyme, comprising:
   a) isolating a DNA sequence encoding the lipolytic enzyme from a lipolytic enzyme-producing strain of Gliocladium, Verticillium or Trichophaea,
   b) combining the DNA fragment with appropriate expression signal(s) in an appropriate vector,
   c) transforming a suitable heterologous host organism with the vector,
   d) cultivating the transformed host organism under conditions leading to expression of the lipolytic enzyme, and
   e) recovering the lipolytic enzyme from the culture medium.

8. An isolated DNA sequence which encodes the lipolytic enzyme of any of claims 1–7.

9. An isolated, lipolytic enzyme encoding DNA sequence which comprises:
   a) the lipolytic enzyme encoding part of the DNA sequence cloned into a plasmid present in *Escherichia coli* DSM 10591, DSM 10590 or DSM 11298, or
   b) the DNA sequence shown in positions 114–713 of SEQ ID NO: 2, positions 133–738 of SEQ ID NO: 5 or positions 161–763 of SEQ ID NO: 7, or
   c) an analogue of the DNA sequence defined in a) or b) which
      i) is at least 60% homologous with said DNA sequence, or
      ii) hybridizes with said DNA sequence at 55° C.

10. A recombinant expression vector comprising the DNA sequence of any of claims 19–24.

11. A cell comprising the DNA sequence of any of claims 19–24 or the recombinant expression vector of claim 25.

12. A method of producing a lipolytic enzyme, comprising culturing the cell of any of claims 26–29 under conditions permitting the production of the enzyme, and recovering the enzyme from the culture.

13. A biologically pure culture of a microbial strain which belongs to the genus Gliocladium or Verticillium and is capable of producing an alkaline lipolytic enzyme.

14. *Escherichia coli* strain DSM 10591, DSM 10590 or DSM 11298 or a mutant thereof having lipolytic enzyme encoding capability.

COMPARISON WITH PRIOR ART

Tilburg and Thomas, Application. Environ. Microbiol., January 1993, p. 236–242 describes production of lipase by *G. virens*; however, data in the article show that the prior-art lipase is not alkaline. U.S. Pat. Nos. 4,985,365 and 4,511,655 describe the use of culture broth of *G. roseum* IFO 5422 and *G. virens* IFO 6355 to hydrolyze carboxylic esters at acid pH. The prior art does not describe the production of lipolytic activity at alkaline pH by strains of Gliocladium.

The prior art describes the production of lipase by *Verticillium cinnabarinum* (also called *V. luteoalbum*) DSM 63078 (Rapp & Backhaus, Enzyme Microb. Technol., 14, 938–943 (1992)) and *Verticillium lecanii* ATCC 26854 (JP-A 61-289884). The inventors have investigated the two strains and found that they do not produce alkaline lipolytic enzyme.

The following literature describes lipase production by the genus Verticillium without identifying any particular strains: Kunert & Lysek, Biologica (Bratislava), 42 (3), 285–293 (1987). Leger et al., J. Invertebr. Pathol., 48, 85–95 (1986). Jackson et al., Ann. appl. Biol., 106, 39–48 (1985). Roberts et al., Mycologia, 79 (2), 265–273 (1987). Trigiano, Mycologia, 71, 908–917 (1979). However, the prior art does not describe the production of lipolytic activity at alkaline pH by strains of Verticillium.

A homology search was performed in nucleotide and protein databases. The highest homology for the lipolytic enzyme and DNA sequences of the invention was found with the sequence for cutinase from *Fusarium solani f.* sp. *pisi*, described by C. L. Soliday et al., Proc. Natl. Acad. Sci. USA, 81, 3939–3943 (1984).

The three DNA sequences of the invention described earlier in this specification show homologies of 53–57% with the above known DNA sequence, and the three amino acid sequences of the invention described earlier show homologies of 50–53% with the above known amino acid sequence. The calculation of homology was done as described later in this specification. Using a formula given in "Current Protocols in Molecular Biology", John Wiley & Sons, 1995, hybridization of the above DNA of the invention and the closest prior-art DNA is estimated to have a melting temperature of 50° C. at the hybridization conditions given later in this specification.

BRIEF DESCRIPTION OF THE DRAWINGS

FIGS. 1–7 show pH-activity curves for lipolytic enzymes from the following strains. The pH curves were made with purified enzyme samples, except that those in FIGS. 3–5 were made with crude enzyme samples.

FIG. 1: Gliocladium sp. NN140631

FIG. 2: *G. solani* NN102998

FIG. 3: *G. roseum* NN141784

FIG. 4: *G. aureum* NN102987

FIG. 5: *G. roseum* NN141961

FIG. 6: Verticillium sp. CBS 830.95

FIG. 7: *T. saccata* CBS 804.70

FIG. 8 shows the stability at various temperatures for the lipolytic enzyme from Verticillium sp. CBS 830.95.

DETAILED DISCLOSURE OF THE INVENTION

Lipolytic Enzymes

The enzymes of this invention are lipolytic enzymes. In the present context the term "lipolytic enzyme" is intended to indicate an enzyme classified under the Enzyme Classification number E.C. 3.1.1.- (Carboxylic Ester Hydrolases) in accordance with the Recommendations (1992) of the International Union of Biochemistry and Molecular Biology (IUBMB). Lipolytic enzymes thus exhibit hydrolytic activity towards at least one of the types of ester bonds mentioned in the context of E.C. 3.1.1.

The lipolytic enzymes of the invention preferably have lipase activity (with triglycerides as substrate) and/or cutinase activity (with cutin as substrate, as described in Kolattukudy, Science, vol. 208, May 30, 1980, pp. 990–1000 and Kolattukudy in "Lipases", Borgström and Brockman ed., Elsevier 1984, pp. 471–504).

Properties of Lipolytic Enzyme

The invention provides lipolytic enzymes having a high activity at alkaline pH in the absence of $Ca^{++}$. Preferably, the alkaline lipolytic enzyme of the invention has a lipolytic activity at pH 10 in the absence of $Ca^{++}$ above 20% (most preferably above 50%) of the lipolytic activity at pH 10 in the presence of 50 mM $Ca^{++}$. And preferably, the lipolytic enzymes have a lipolytic activity at pH 10 in the absence of $Ca^{++}$ above 50% of the activity at pH 8 as well as pH 9 in the absence of $Ca^{++}$. Such an enzyme can be obtained from a strain of Gliocladium.

Figure 1:
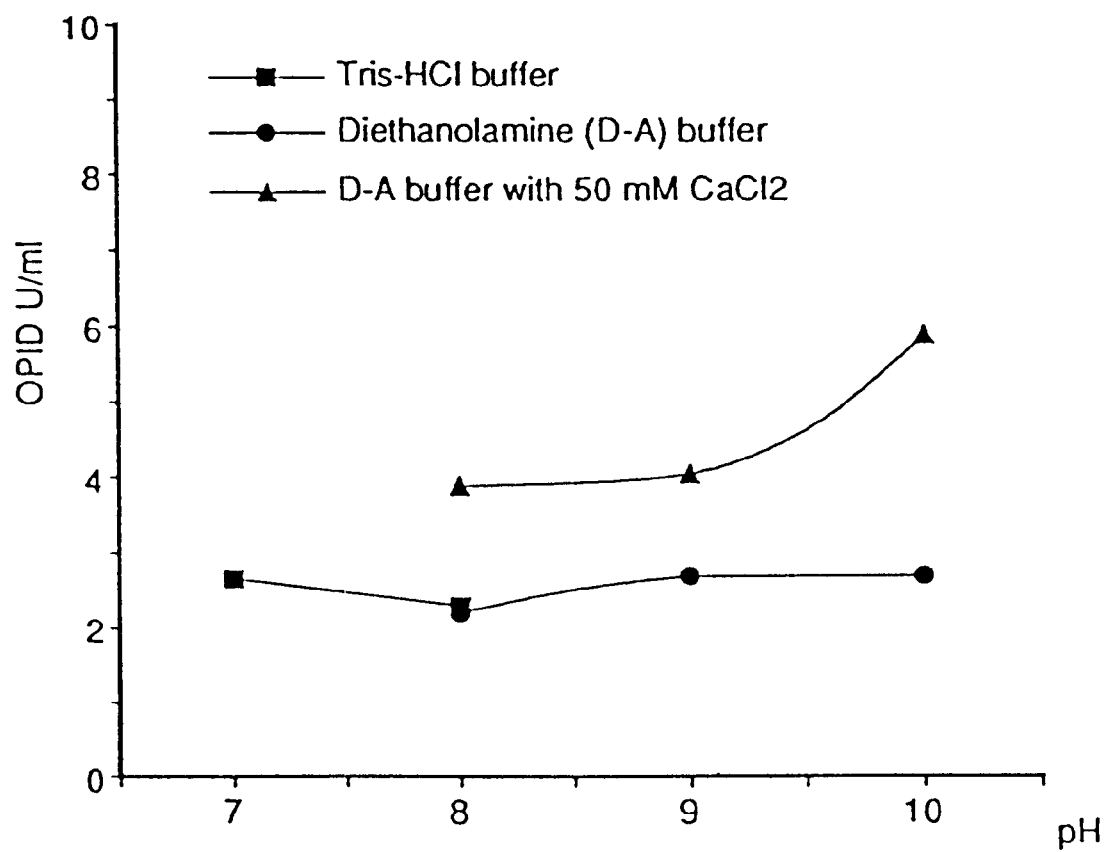
Figure 2:
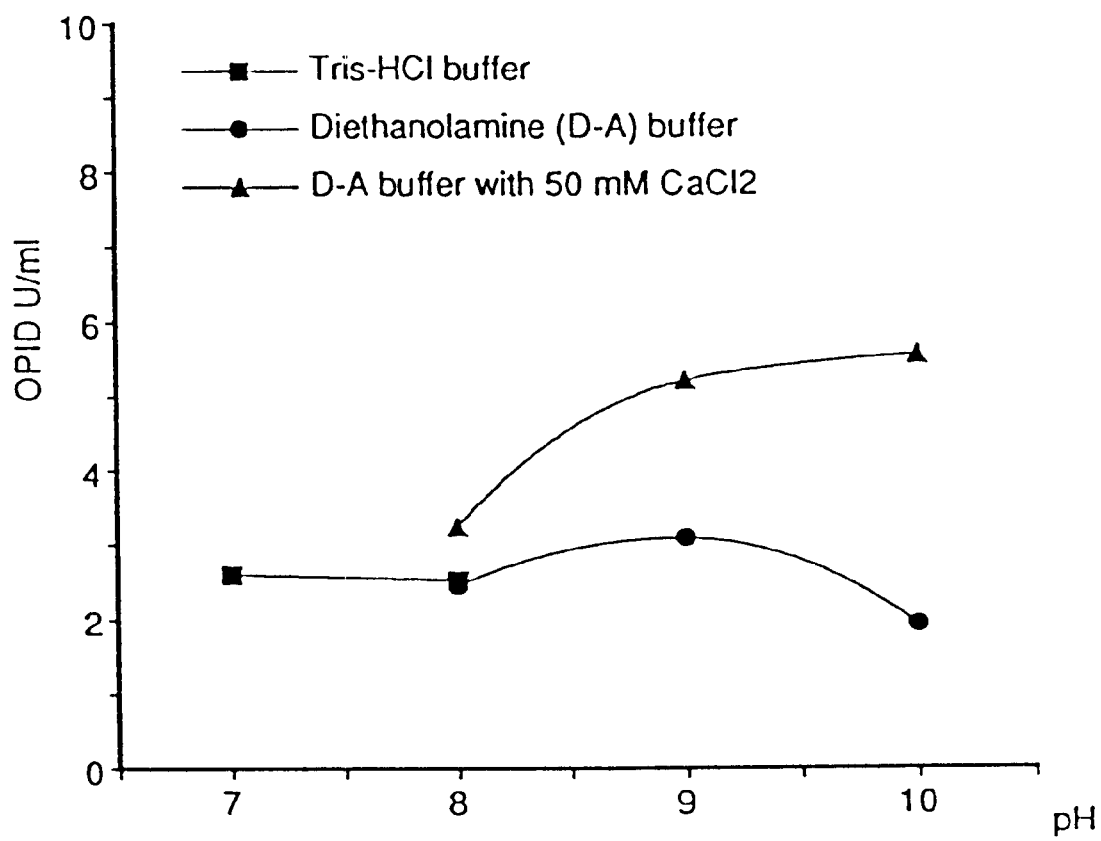
Figure 3:
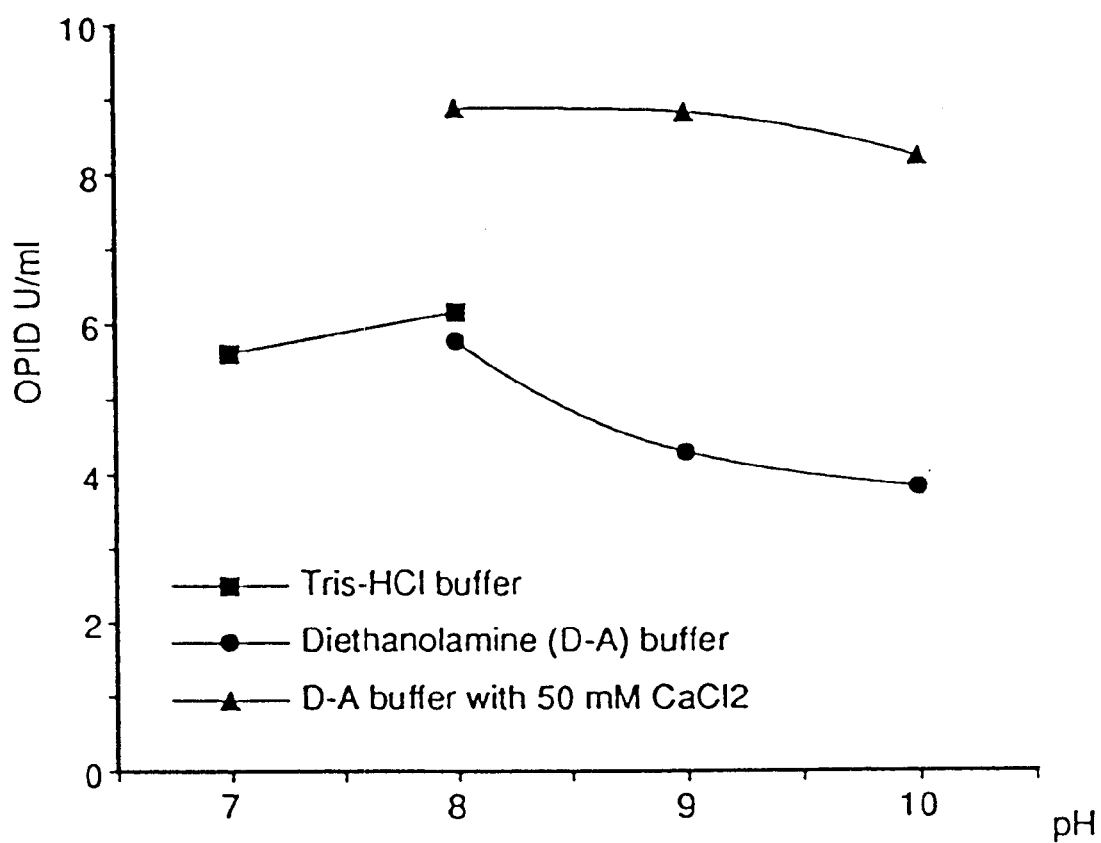
Figure 4:
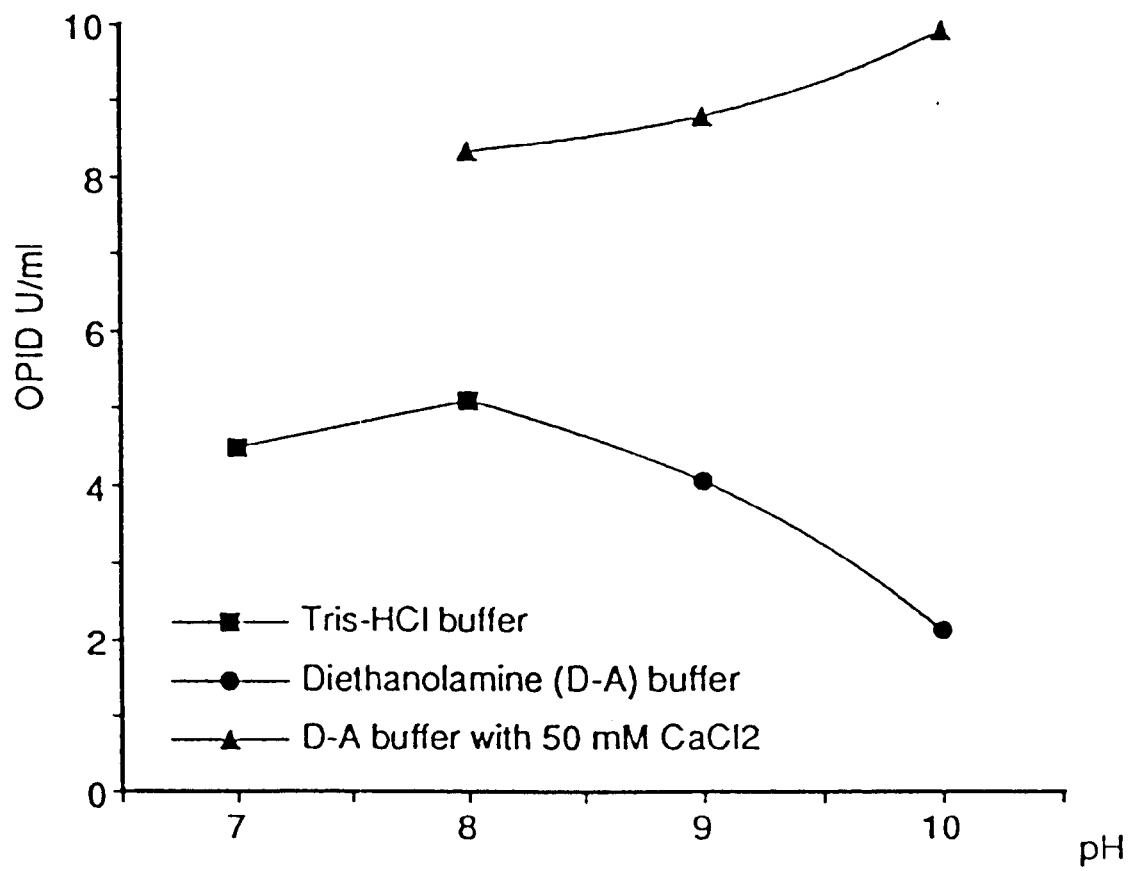
Figure 5:
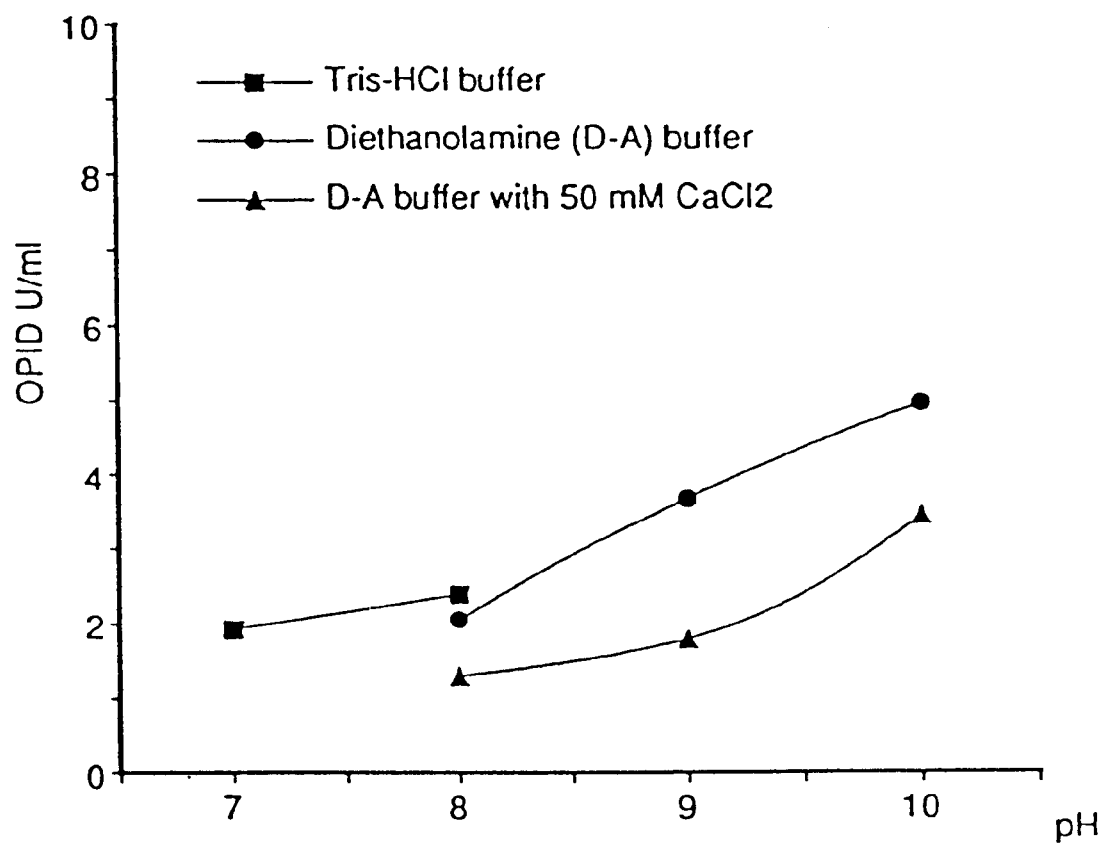

Curves of lipolytic activity versus pH with and without addition of $Ca^{++}$ are shown in FIGS. 1–7 for lipolytic enzymes according to the invention from the following strains: Gliocladium sp. NN140631, *G. solani* NN102998, *G. roseum* NN141784, *G. aureum* NN102987, *G. roseum* NN141961, Verticillium sp. CBS 830.95 and *T. saccata* CBS 804.70. The activity was determined by the OPID method described later in this specification (except that 60 minutes incubation was used for the data in FIG. 4). The pH curves were made with purified enzyme samples, except that those in FIGS. 3–5 were made with crude enzyme samples.

Advantageously, the lipolytic enzymes of the invention are active throughout the pH range 8–10. Some preferred enzymes have increasing activity up to pH 10, indicating a pH optimum above 10.

The specific lipolytic enzyme activity is 1800 LU per $A_{280}$ for the lipolytic enzyme from Verticillium sp. CBS 830.95. The specific activity is expressed as lipase activity (LU) per mg of protein determined from absorption at 280 nm.

The stability is shown in FIG. 8, as expressed by the residual activity after incubating the lipolytic enzyme from Verticillium sp. CBS 830.95 at various temperatures for 30 minutes at pH 9. The enzyme is fully stable for 30 minutes at pH 9 at temperatures up to 50° C. This enzyme was also found to be fully stable throughout the pH range 6–10 at 25° C. for 24 hours.

The invention also provides lipolytic enzymes having a high stability in a detergent solution. Preferably, the alkaline lipolytic enzyme of the invention retains more than 90% activity after 30 minutes incubation in 100 mM glycine at pH 10, 45° C. or in the test detergent solution shown in the Examples at pH 10.2, 40° C. The lipolytic enzymes of the enzymes furthermore show a good washing performance on fatty soiling during the washing of textiles with detergent. Preferably, the alkaline lipolytic enzyme of the invention gives a degree of hydrolysis above 15% (most preferably above 20%) on cotton/olive oil swatches in the Activity-in-Detergent (AiD) assay described later in this specification. Such an enzyme can be obtained from a strain of Verticillium.

In this specification, lipolytic enzyme activity is expressed in units of LU, OPIDU and SLU determined by the methods described below.

Characterization of Enzyme Protein

The iso-electric point was determined by iso-electric focusing for some lipolytic enzymes according to the invention, as follows:

| Organism | Strain No. | Iso-electric point |
|---|---|---|
| G. solani | NN102998 | 5.4 |
| Gliocladium sp. | NN140631 | 9.3 |
| Verticillium sp. | CBS 830.95 | 6.0 |

The molecular weight (MW) was determined by SDS-PAGE and by mass spectrometry for some lipolytic enzymes according to the invention, as follows:

| Organism | Strain No. | MW (SDS-PAGE) | MW (mass spectrometry) |
|---|---|---|---|
| G. solani | NN102998 | 22 kDa | 20,989 ± 21 Da |
| Verticillium sp. | CBS 830.95 | 22 kDa | 21,107 ± 21 Da |

The N-terminal sequence of the lipolytic enzyme from *G. solani* NN102998 was determined for 35 residues as shown in SEQ ID NO: 1. The complete amino acid sequence of the lipolytic enzyme from Gliocladium sp. CBS 173.96 was deduced from the determination of the DNA sequence and is shown in positions 1–200 of SEQ ID NO: 3. A comparison of the two amino acid sequences shows that the first 35 amino acids of the two enzymes are identical, except for position 20.

The N-terminal sequence determined for the lipolytic enzyme from Verticillium sp. CBS 830.95 is shown in SEQ ID NO: 4 (positions 1–29); Xaa indicates an undetermined amino acid. The complete amino acid sequence of this enzyme, as deduced from the DNA sequence, is shown in positions 1–202 of SEQ ID NO: 6.

The amino acid sequence of the lipolytic enzyme from *T. saccata* CBS 804.70 shown in positions 1–201 of SEQ ID NO: 8 was deduced from the DNA sequence, and the position of the N-terminal was deduced by a comparison with the highly homologous sequence from Gliocladium sp. CBS 173.96.

Lipolytic Activity by the LU Method

One Lipase Unit (LU) is the amount of enzyme which liberates 1 $\mu$mol of titratable fatty acid per minute with tributyrin as substrate and gum arabic as emulsifier at 30.0° C., pH 7.0 (phosphate buffer).

Lipase Activity by the OPID Method

The lipolytic enzyme activity without free $Ca^{++}$ in the range pH 7–10 is tested with a substrate emulsion of olive oil: 2% PVA solution (1:3) at 40° C. for 10 minutes, at a specified pH. At the end of the reaction, the reaction mixture is extracted by chloroform:methanol (1:1) at acidic conditions, and the fatty acid released during the reaction is measured by TLC-FID analysis (Iatroscan). One unit (OPIDU) is taken as the release of a $\mu$mole of fatty acid per minute.

In each test, 10 mM EDTA is used together with 200 mM of buffer (Tris-HCl buffer at pH 7 and 8, diethanol amine buffer at pH 8, 9 and 10).

Lipolytic Activity by the SLU Method

The lipolytic activity may be determined using olive oil as substrate. In this SLU method, the lipase activity is measured at 30° C. and pH 9 with a stabilized olive oil emulsion (Sigma catalog No. 800-1) as the substrate, in a 5 mM Tris buffer containing 40 mM NaCl and 5 mM calcium chloride. 2.5 ml of the substrate is mixed with 12.5 ml buffer, the pH is adjusted to 9, 0.5 ml of diluted lipase sample is added, and the amount of oleic acid formed is followed by titration with a pH stat.

One SLU is the amount of lipase which liberates 1 $\mu$mole of titratable oleic acid per minute under these conditions.

Activity-in-Detergent (AiD) Assay

Equipment: Water bath with 150 ml beakers. Stirring is obtained by an agitator.

Lipolytic enzyme dosage: 0 & 12500 LU/l.

Substrate: 6 pieces (3.5*3.5 cm) of cotton with 6 $\mu$l olive oil

Detergent: 0.5 g/l model liquid detergent (see below) dissolved in 0,36 mM $Ca^{2+}/Mg^{2+}$ (5:1), adjusted to pH 10. 100 ml per beaker.

Method: The test swatches are added to the detergent solution, after which the samples get stirred for 60 min at 30° C. The remaining detergent on the swatches gets removed by rinsing in tap water for 15 min. The swatches are put into a flask containing 10 ml tetrahydrofuran and 6.25 µl 4 M HCl and evaporated over night, after which the samples are redissolved in tetrahydrofuran. The effect of the lipolytic enzyme is determined:

By measuring the degree of hydrolysis (% DH) by an latroscan TLC/FID method

Model Liquid Detergent

| Component | Model detergent, % w/w |
|---|---|
| Linear alkylbenzene sulfate (LAS) | 17.5 |
| Alcohol ethoxylate (AEO) | 14.4 |
| Dodecenyl/tetradecenyl succinic acid (DTSA) | 10 |
| Oleic acid | 3 |
| Coconut oil | 5 |
| Mono ethanol amine (MEA) | 14.5 |
| Mono propylene glycol (MPG) | 10.7 |
| Ethanol | 1.4 |
| Phosphonate | 1.0 |
| Boric acid | 0.8 |
| Citric acid | 3.9 |
| Sodium chloride | 0.13 |
| Potassium chloride | 0.38 |
| Hydrochloric acid 4 M | 6 |
| Water | 9.7 |
| pH adjusted to (5 g/l) | 7.7 |

Microbial Sources

The lipolytic enzyme of this invention may be derived from an ascomycete of the order Hypocreales which belongs to the genus Gliocladium, Verticillium or Trichophaea.

The genus Gliocladium is characterized by having one-celled conidia formed from phialides in slimy heads. The conidiophores are distinctly penicillate. It is described in Domsch K. H. & Gams W. (1993) Compendium of Soil Fungi (reprint of 1980 edition), Volume I, IHW-Verlag, page 368.

The genus Verticillium is characterized by predominantly hyaline hyphae with well differentiated erect conidiophores that are verticillately branched. The branches bear whorls of slender phialides from which hyaline or brightly colored conidia are formed. The conidial masses are seen as slimy heads on top of the phialidia.

The following species and strains are preferred. Variants and mutants thereof capable of producing lipolytic enzyme may also be used in the invention.

| Species name | Inventors' strain No. | Deposit number | Deposit date |
|---|---|---|---|
| Gliociadium sp. | NN140531 | CBS 173.96 | February 5, 1996 |
| G. ammoniophilum | NN102992 | CBS 156.70 | |
| G. aureum | NN102987 | IFO 9055 | |
| G. catenulatum | NN100802 | ATCC 10523 | |
| G. flavum | NN102995 | CBS 155.27 | |
| G. nigrovirens | NN102996 | CES 183.30 | |
| G. roseum | NN141784 | CBS 126.96 | January 22, 1998 |
| | NN141961 | CBS 127.96 | January 22, 1996 |
| G. sagariensis | NN102989 | IFO 9080 | |
| G. solani | NN102998 | CBS 707.86 | |
| Verticillium sp. | NN001755 | CBS 830.95 | 22 December 1995 |
| T. saccata | NN102806 | CES 804.70 | |

The deposit numbers in the above list refer to deposits made at the following deposit institutions:

CBS: Centraal Bureau voor Schimmelcultures, Oosterstraat 1, 3740 AG Baarn, Netherlands.

IFO: Institute for Fermentation, 17–85 Juso-honmachi 2-chome, Yodogawa-ku, Osaka 532, Japan.

NRRL: Agricultural Research Service Culture Collection (NRRL), 1815 North University Street, Peoria, Ill. 61604, USA.

The following strains were isolated by the inventors: Gliocladium sp. CBS 173.96, G. roseum CBS 126.96, G. roseum CBS 127.96 and Verticillium sp. CBS 830.95. These strains were deposited by the inventors according to the Budapest Treaty on the International Recognition of the Deposit of Microorganisms for the Purposes of Patent Procedure with the deposit numbers and dates given in the table above. They were classified by standard taxonomic methods. Two strains are denoted as "sp.", indicating that they could not be identified to species level. Verticillium sp. CBS 830.95 was isolated from leaf-material and thus most likely belongs to the group of saprophytic species on plant material.

Transformant E. coli Strains

Expression plasmids comprising the full length cDNA sequence encoding lipolytic enzymes of the invention from three of the above strains were transformed into strains of Escherichia coli as indicated earlier in this specification. The transformants were deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, (DSM). The deposit numbers and dates of the transformed E. coli strains were as follows:

| Deposit number | Deposit date |
|---|---|
| DSM 10591 | 15 March 1996 |
| DSM 10590 | 15 March 1996 |
| DSM 11298 | 27 November 1996 |

DNA Sequence

In this specification and claims, whenever reference is made to the lipolytic enzyme encoding part of the DNA sequence cloned into a plasmid present in a transformed E. coli strain, such reference is also intended to include the lipolytic enzyme encoding part of the corresponding DNA sequence listing as identified earlier in this specification. Accordingly, the terms may be used interchangeably.

The DNA sequence of the invention may be isolated from the deposited transformant of Escherichia coli by extraction of plasmid DNA by methods known in the art (Sambrook et al. (1989) Molecular cloning: A laboratory manual, Cold Spring Harbor lab., Cold Spring Harbor, N.Y.).

The DNA sequence of the invention may also be isolated from a strain of the genus Gliocladium, Verticillium or Trichophaea producing the lipolytic enzyme of the invention or another or related organism and thus, e.g. be an allelic or species variant of the lipolytic enzyme encoding part of the DNA sequence cloned into a plasmid present in a transformant of Escherichia coli identified earlier in this specification.

Alternatively, the sequence may be constructed on the basis of the DNA sequence presented as the lipolytic enzyme encoding part of the indicated sequence listings, e.g., it may be a sub-sequence thereof, and/or be derived by introduction of nucleotide substitutions which do not give rise to another amino acid sequence of the lipolytic enzyme encoded by the DNA sequence, but which corresponds to the codon usage of the host organism intended for production of the enzyme, or by introduction of nucleotide substitutions which may give rise to a different amino acid sequence.

When carrying out nucleotide substitutions, amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain.

Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford et al., (1991), Protein Expression and Purification 2, 95–107.

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (cf. e.g. Cunningham and Wells, (1989), Science 244, 1081–1085). In the latter technique mutations are introduced at every residue in the molecule, and the resultant mutant molecules are tested for biological (i.e. lipolytic enzyme) activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labeling (cf. e.g. de Vos et al., (1992), Science 255, 306–312; Smith et al., (1992), J. Mol. Biol. 224, 899–904; Wlodaver et al., (1992), FEBS Lett. 309, 59–64).

The DNA sequence of the invention can be isolated from the transformed E. coli strain by extraction of DNA by methods known in the art, e.g. as described by Sambrook et al., (1989), Molecular Cloning: A Laboratory Manual. Cold Spring Harbor Lab.; Cold Spring Harbor, N.Y.

The DNA sequence of the invention can also be isolated by any general method involving cloning, in suitable vectors, a cDNA library from any organism expected to produce the lipolytic enzyme of interest, transforming suitable yeast host cells with said vectors, culturing the host cells under suitable conditions to express any enzyme of interest encoded by a clone in the cDNA library, screening for positive clones by determining any lipolytic enzyme activity of the enzyme produced by such clones, and isolating the enzyme encoding DNA from such clones.

A general isolation method has been disclosed in WO 93/11249 or WO 94/14953, the contents of which are hereby incorporated by reference. A more detailed description of the screening method is given in the Examples below.

Alternatively, the DNA encoding a lipolytic enzyme of the invention may, in accordance with well-known procedures, conveniently be isolated from a suitable source, such as the microorganisms described above, by use of synthetic oligonucleotide probes prepared on the basis of a DNA sequence disclosed herein. For instance, a suitable oligonucleotide probe may be prepared on the basis of the lipolytic enzyme encoding part of the nucleotide sequences presented as SEQ ID NO: 2 or any suitable subsequence thereof, or on the basis of the amino acid sequence SEQ ID NO: 3.

Homology of DNA Sequences

The DNA sequence homology referred to in this specification with claims is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711; Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the coding region of the analogous DNA sequences referred to above exhibits a degree of identity preferably of at least 70%, more preferably at least 80%, more preferably at least 90%, more preferably at least 95%, more preferably at least 97% with the lipolytic enzyme encoding part of the DNA sequence indicated earlier in the specification.

Hybridization

The hybridization referred to above is intended to indicate that the analogous DNA sequence hybridizes to the same probe as the DNA sequence encoding the lipolytic enzyme under certain specified conditions which are described in detail below. The oligonucleotide probe to be used is the DNA sequence corresponding to the lipolytic enzyme encoding part of the DNA sequence listings indicated earlier in the specification.

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 $\mu$g/ml of denatured sonicated salmon sperm DNA (Sambrook et al. 1989), followed by hybridization in the same solution containing a random-primed (Feinberg, A. P. and Vogelstein, B. (1983) Anal. Biochem. 132:6–13), $^{32}$P-dCTP-labeled (specific activity>1×10$^9$ cpm/$\mu$g ) probe for 12 hours at ca. 45° C. The filter is then washed two times for 30 minutes in 2×SSC, 0.5% SDS at temperatures up to 55° C., preferably up to 60° C., more preferably up to 65° C., even more preferably up to 70° C., and especially up to 75° C.

Molecules to which the oligonucleotide probe hybridizes under these conditions are detected using a x-ray film.

Homology of Amino Acid Sequences

The polypeptide homology referred to in this specification with claims is determined as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711; Needleman, S. B. and Wunsch, C. D., (1970), Journal of Molecular Biology, 48, 443–453). Using GAP with the following settings for polypeptide sequence comparison: GAP creation penalty of 3.0 and GAP extension penalty of 0.1, the mature part of a polypeptide encoded by an analogous DNA sequence exhibits a degree of identity preferably of at least 70%, more preferably at least 80%, more preferably at least 90%, more preferably at least 95%, and especially at least 97% with the mature part of the amino acid sequence of lipolytic enzymes indicated earlier in this specification.

Immunological Cross-reactivity

Antibodies to be used in determining immunological cross-reactivity may be prepared by use of a purified lipolytic enzyme. More specifically, antiserum against the lipolytic enzyme of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation ((NH4)2 SO4), followed by dialysis and ion exchange chromatography, e.g. on DEAE-Sephadex. Immunochemical characterization of proteins may be done either by Ouchterlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Expression Vectors

The expression vector of the invention may be any expression vector that is conveniently subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector, the DNA sequence encoding the lipolytic enzyme should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the lipolytic enzyme, the promoter and the terminator, respectively, and to insert them into suitable vectors are well known to persons skilled in the art (cf., for instance, Sambrook et al., (1989), Molecular Cloning. A Laboratory Manual, Cold Spring Harbor, N.Y.).

Examples of suitable promoters for use in filamentous fungus host cells are, for instance, the ADH3 promoter (McKnight et al., The EMBO J. 4 (1985), 2093–2099) or the tpiA promoter. Examples of other useful promoters are those derived from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (gluA), *Rhizomucor miehei* lipase, *Aspergillus oryzae* alkaline protease, *Aspergillus oryzae* triose phosphate isomerase or *Aspergillus nidulans* acetamidase.

Host Cells

The host organism is preferably a eukaryotic cell, in particular a fungal cell, such as a yeast cell or a filamentous fungal cell. Preferred filamentous fungi include Aspergillus, Fusarium or Trichoderma, most preferably *A. niger*, *A. oryzae*, *F. graminearum*, *F. sambucinum*, *F. cerealis*, *T. harzianum* or *T. reesei*. Fungal cells may be transformed by a process involving protoplast formation and transformation of the protoplasts followed by regeneration of the cell wall in a manner known per se. Protoplasts may be prepared as described in WO 95/02043, p. 16, line 21 –page 17, line 12, which is hereby incorporated by reference. The use of Aspergillus as a host microorganism is described in EP 238 023 (Novo Nordisk A/S), the contents of which are hereby incorporated by reference. The host cell may also be a yeast cell, e.g. a strain of Saccharomyces, in particular *Saccharomyces cerevisiae, Saccharomyces kluyveri* or *Saccharomyces uvarum*, a strain of Schizosaccharomyces such as *Schizosaccharomyces pombe,* a strain of Hansenula, Pichi, Yarrowia (such as *Yarrowia lipolytica*) or Kluyveromyces (such as *Kluyveromyces lactis*).

Production of Lipolytic Enzyme

The lipolytic enzyme of the invention may be produced by cultivation of one of the microorganisms described above in a suitable nutrient medium, containing carbon and nitrogen sources and inorganic salts, followed by recovery of the lipolytic enzyme. An alternative method of producing the lipolytic enzyme of the invention comprises transforming a suitable host cell with a DNA sequence encoding the enzyme, cultivating the transformed organism under conditions permitting the production of the enzyme, recovering the enzyme from the culture.

The medium used to culture the microorganism or transformed host cells may be any conventional medium suitable for growing the organism in question. The expressed lipolytic enzyme may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Application of Lipolytic Enzyme

The lipolytic enzyme of the invention may be used in conventional applications of lipolytic enzyme, particularly at a high pH, e.g. in laundry and dishwash detergents, in institutional and industrial cleaning and in leather processing.

The lipolytic enzymes of the invention can also be used for interesterification, for total hydrolysis of fats and oils and in optical isomer resolution processes.

Detergent Additive

According to the invention, the lipolytic enzyme may typically be used as an additive in a detergent composition. This additive is conveniently formulated as a non-dusting granulate, a stabilized liquid, a slurry or a protected enzyme.

A suitable activity range for a detergent additive containing the lipolytic enzyme of this invention is 5,000–100,000 OPIDU/g (OPID measured at pH 9) or 0.01–100 mg pure enzyme protein per g of the additive.

Detergent

The lipolytic enzyme of the invention may be incorporated in concentrations conventionally employed in detergents. The detergent composition of the invention may comprise lipolytic enzyme in an amount corresponding to 10–50,000 LU per gram of detergent, preferably 20–5,000

LU/g. The detergent may be dissolved in water to produce a wash liquor containing lipolytic enzyme in an amount corresponding to 25–15,000 LU per liter of wash liquor. The amount of lipolytic enzyme protein may be 0.001–10 mg per gram of detergent or 0.001–100 mg per liter of wash liquor.

Detergent Compositions

According to the invention, the lipolytic enzyme may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or non-aqueous.

The detergent composition comprises one or more surfactants, each of which may be anionic, nonionic, cationic, or zwitterionic. The detergent will usually contain 0–50% of anionic surfactant such as linear alkylbenzene sulfonate (LAS), alpha-olefin sulfonate (AOS), alkyl sulfate (fatty alcohol sulfate) (AS), alcohol ethoxysulfate (AEOS or AES), secondary alkane sulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylase, cutinase, protease, cellulase, peroxidase, and oxidase, e.g., laccase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethyl cellulose (CMC), poly(vinyl pyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzene sulfonate (NOBS). Alternatively, the bleaching system may comprise peroxy acids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzene sulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O,2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBo_3 \cdot H_2O$) | 11–18% |
| TAED | 2–6% |
| Carboxymethyl cellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzene sulfonate (calculated as acid) | 6–11% |
| Alcohol ethoxysulfate (e.g. $C_{12-18}$ alcohol, 1–2 EO) or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O,2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethyl cellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| Linear alkylbenzene sulfonate (calculated as acid) | 5–9% |
|---|---|
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O,2SiO_2$) | 3–9% |
| Zeolite (as $NaAlSiO_4$) | 23–33% |
| Sodium sulfate (as $Na_2SO_4$) | 0–4% |
| Sodium perborate (as $NaBo_3.H_2O$) | 8–16% |
| TAED | 2–8% |
| Phosphonate (e.g. EDTMPA) | 0–1% |
| Carboxymethyl cellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| Linear alkylbenzene sulfonate (calculated as acid) | 8–12% |
|---|---|
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O,2SiO_2$) | 1–5% |
| Zeolite (as $NaAlSiO_4$) | 25–35% |
| Sodium sulfate (as $Na_2SO_4$) | 0–10% |
| Carboxymethyl cellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| Linear alkylbenzene sulfonate (calculated as acid) | 15–21% |
|---|---|
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants, suds suppressors, perfume, optical brightener) | 0–5% |

6) An aqueous structured liquid detergent composition comprising

| Linear alkylbenzene sulfonate (calculated as acid) | 15–21% |
|---|---|
| Alcohol ethoxylate (e.g. $C_{12-15}$ alcohol, 7 EO or $C_{12-15}$ alcohol, 5 EO) | 3–9% |
| Soap as fatty acid (e.g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethyl cellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

7) A detergent composition formulated as a granulate having a bulk density of at least 600 g/l comprising

| Fatty alcohol sulfate | 5-10% |
|---|---|
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O,2SiO_2$) | 1–4% |
| Zeolite (as $NaAlSiO_4$) | 20–40% |
| Sodium sulfate (as $Na_2SO_4$) | 2–8% |
| Sodium perborate (as $NaBo_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| Linear alkylbenzene sulfonate (calculated as acid) | 8–14% |
|---|---|
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O,2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| Linear alkylbenzene sulfonate (calculated as acid) | 6–12% |
|---|---|
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaB_O3.H_2O$) | 4–9% |
| Bleach activator (e.g. NOBS or TAED) | 1–5% |
| Carboxymethyl cellulose | 0–2% |
| Polymers (e.g. polydarboxylate or PEG) | 1–5% |
| Enzymes (calculated as pure enzyme protein) | 0.0001–0.1% |
| Minor ingredients (e.g. optical brightener, perfume) | 0–5% |

10) An aqueous liquid detergent composition comprising

| Linear alkylbenzene sulfonate (calculated as acid) | 15–23% |
|---|---|
| Alcohol ethoxysulfate (e.g. $C_{12-15}$ alcohol, 2–3 EO) | 8–15% |
| Alcohol ethoxylate (e.g. $C_{12-15}$ alcohol, 7 EO, or $C_{12-15}$ alcohol, 5 EO) | 3–9% |
| Soap as fatty acid (e.g. lauric acid) | 0–3% |
| Aminoethanol | 1–5% |
| Sodium citrate | 5–10% |

-continued

| | |
|---|---|
| Hydrotrope (e.g. sodium toluene sulfonate) | 2–6% |
| Borate (as $B_4O_7$) | 0–2% |
| Carboxymethyl cellulose | 0–1% |
| Linear alkylbenzene sulfonate (calculated as acid) | 15–23% |
| Ethanol | 1–3% |
| Propylene glycol | 2–5% |
| Enzymes (calculated as pure enzyme protein) | 0.0001–0.1% |
| Minor ingredients (e.g. polymers, dispersants perfume, optical brighteners) | 0–5% |

11) An aqueous liquid detergent composition comprising

| | |
|---|---|
| Linear alkylbenzene sulfonate (calculated as acid) | 20–32% |
| Alcohol ethoxylate (e.g. $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzene sulfonate, alkyl sulfate, alpha-olefin sulfonate, alpha-sulfo fatty acid methyl esters, alkane sulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O,2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3 \cdot 4H_2O$) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzene sulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g. SK56 from Hoechst) | 10–20% |
| Sodium carbonate (as $Na_2CO_3$) | 3–12% |
| Soluble silicates (as $Na_2O,2SiO_2$) | 0–6% |
| Sodium citrate | 4–8% |
| Sodium percarbonate | 13–22% |
| TAED | 3–8% |
| Polymers (e.g. polycarboxylates and PVP=) | 0–5% |
| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O,2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The lipolytic enzyme of the invention may be incorporated in concentrations conventionally employed in detergents. It is at present contemplated that, in the detergent composition of the invention, the lipolytic enzyme may be added in an amount corresponding to 0.00001–1 mg (calculated as pure enzyme protein) of lipolytic enzyme per liter of wash liquor.

EXAMPLES

Materials and Methods

The following materials and methods were used in the Examples that follow:

Microorganisms

Yeast strain: The *Saccharomyces cerevisiae* strain used was W3124 (MATα; ura 3–52; leu 2–3, 112; his 3-D200; pep 4-1137; prc1::HIS3; prb1:: LEU2; cir+).

*E. coli* strain: DH10B (available, e.g., from Life Technologies)

Plasmids

The Aspergillus expression vector pHD414 is a derivative of the plasmid p775 (described in EP 238 023). The construction of pHD414 is further described in WO 93/11249.

pYES 2.0 (available, e.g., from Invitrogen)

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Expression Cloning in Yeast

Expression cloning in yeast was done as comprehensively described by H. Dalboege et al. (H. Dalboege et al Mol. Gen. Genet (1994) 243:253–260.; WO 93/11249; WO 94/14953), which are hereby incorporated as reference.

Extraction of total RNA, cDNA synthesis, Mung bean nuclease treatment, Blunt-ending with T4 DNA polymerase, and Construction of libraries were done according to the references mentioned above.

Identification of Positive Clones

The transformants are plated on SC agar containing 2% glucose and incubated for 3 days at 30° C. A cellulose acetate filter (OE 67, Schleicher & Schuell) is placed on top of the cells and then transferred to plates containing SC agar and 2% galactose with the cells on the top of the filter. After 3 days of incubation at 30° C. the filter with cells is transferred to substrate plates. Positive clones are identified as colonies surrounded by a green zone.

Characterization of Positive Clones

The positive clones are obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al. (1977) Proc. Natl. Acad. Sci. U.S.A. 74:5463–5467) and the Sequenase system (United States Biochemical).

Isolation of a cDNA Gene for Expression in Aspergillus

A lipolytic enzyme-producing yeast colony is inoculated into 20 ml YPD broth in a 50 ml glass test tube. The tube is shaken for 2 days at 30° C. The cells are harvested by centrifugation for 10 min. at 3000 rpm.

DNA is isolated according to WO 94/14953 and dissolved in 50 $\mu$l water. The DNA is transformed into *E. coli* by standard procedures. Plasmid DNA is isolated from *E. coli* using standard procedures, and analyzed by restriction enzyme analysis. The cDNA insert is excised using appropriate restriction enzymes and ligated into an Aspergillus expression vector.

Transformation of *Aspergillus oryzae* or *Aspergillus niger*

100 $\mu$l of protoplast suspension is mixed with 5–25 $\mu$g of the appropriate DNA in 10 $\mu$l of STC (1.2 M sorbitol, 10 mM Tris-HCl, pH=7.5, 10 mM $CaCl_2$). Protoplasts are mixed with p3SR2 (an *A. nidulans* amdS gene carrying plasmid). The mixture is left at room temperature for 25 minutes. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates (Cove, Biochem. Biophys. Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* Transformants

Each of the transformants is inoculated in 10 ml of YPM (cf. below) and propagated. After 2–5 days of incubation at 30° C., the supernatant is removed. The lipolytic activity is identified by applying 10 $\mu$l supernatant to 4 mm diameter holes punched out in agar plates containing 0.1 M glycine pH 9, 0.1 M $CaCl_2$, 1% Triton X-100, 0.5% olive oil. Lipolytic activity is indicated by the formation of a turbid halo.

Fed Batch Fermentation

Fed batch fermentation was performed in a medium comprising maltodextrin as a carbon source, urea as a nitrogen source and yeast extract. The fed batch fermentation was performed by inoculating a shake flask culture of *A. oryzae* host cells in question into a medium comprising 3.5% of the carbon source and 0.5% of the nitrogen source. After 24 hours of cultivation at pH 7.0 and 34° C. the continuous supply of additional carbon and nitrogen sources were initiated. The carbon source was kept as the limiting factor and it was secured that oxygen was present in excess. The fed batch cultivation was continued for 4 days.

Media

YPD: 10 g yeast extract, 20 g peptone, $H_2O$ to 900 ml. Autoclaved, 100 ml 20% glucose (sterile filtered) added.

YPM: 10 g yeast extract, 20 g peptone, $H_2O$ to 900 ml. Autoclaved, 100 ml 20% maltodextrin (sterile filtered) added.

10×Basal salt: 75 g yeast nitrogen base, 113 g succinic acid, 68 g NaOH, $H_2O$ ad 1000 ml, sterile filtered.

SC-URA: 100 ml 10×Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-agar: SC-URA, 20 g/l agar added.

SC-variant agar: 20 g agar, 20 ml 10×Basal salt, $H_2O$ ad 900 ml, autoclaved

Substrate plates: Petri dish containing 100 mM glycine, pH 9.0, 1% brilliant green solution, 2.5 mM $CaCl_2$, 0.6% olive oil, 0.036% polyvinyl alcohol (MW 70,000–100,000, Sigma P-1763)

PEG 4000 (polyethylene glycol, molecular weight=4,000) (BDH, England)

| | Composition of medium (g/l) | | | | | |
|---|---|---|---|---|---|---|
| Ingredient | Agar30 | YS-2 | Gli | MT-C | NOMO 16 | YS-25 |
| Peptone | 6 | 10 | 10 | 5 | 6 | 10 |
| Pepticase | 4 | | | | 4 | |
| Soybean powder | | | | 30 | | |
| Corn steep powder | | | | 5 | | |
| Yeast extract | 3 | 10 | | 1 | 3 | 10 |
| Meat extract | 1.5 | | | | 1.5 | |
| Glucose | 1 | 20 | | 10 | 1 | 5 |
| $NH_4NO_3$ | | | | 2.5 | | |
| $K_2HPO_4$ | | 5 | 5 | 4 | | 5 |
| $MgSO_4 \cdot 7H_2O$ | | 1 | 1 | 0.1 | | 1 |
| Olive oil | 20 | | 20 | | | |
| Corn oil | | | | 10 or 20 | | |
| Soybean oil | | | | | | 20 |
| Sorbitan monostearate | | | | | 20 | |
| pH adjusted to | 7.4 | 6.5 | 7.0 | 7.0 | 7.4 | 6.5 |

Example 1

Lipase Production from Strains of Gliocladium and Trichophaea

Each of the Gliocladium strains shown in the table below was used for lipolytic enzyme production by a seed culture followed by a main culture. The seed culture was made by cultivation on YS-2 medium for 2 days at 27° C., and the main culture was made at 27° C. using the medium and culture time shown below. At the end of the main culture, the cells were removed and the yield of lipolytic activity was measured using the LU and SLU assay methods.

|  |  |  |  | Lipase activity | |
|---|---|---|---|---|---|
| Species | Strain | Main culture Medium | Days | LU/ml | SLU/ml |
| G. catenulatum | NN100802 | MT-O | 5 | 2.3 | — |
| G. aureum | NN102987 | Agar30 | 3 | 2.4 | 1.7 |
| G. sagariensis | NN102989 | MT-C | 3 | 0.7 | 1.2 |
| G. ammoniophilum | NN102992 | Agar30 | 3 | 3.0 | 2.7 |
| G. flavum | NN102995 | Gli | 3 | 2.1 | 1.5 |
| G. nigrovirens | NN102996 | Gli | 3 | 3.2 | 0.9 |
| G. solani | NN102998 | Agar30 | 5 | 36.0 | — |
| Gliocladium sp. | NN140631 | Agar30 | 3 | 4.4 | — |
| G. roseum | NN141784 | Agar30 | 5 | 2.6 | — |
| G. roseum | NN141961 | MR-10 | 3 | 9.0 | — |
| T. saccata | NN102806 | YS-25 | 3 | 5.2 | — |

All the above strains were seen to produce lipolytic enzyme. A particularly high yield was found by cultivation of G. solani.

Example 2
Activity of Lipolytic Enzymes from Gliocladium and Trichophaea at Various pH The cell-free culture broths from Example 1 were tested for lipolytic enzyme activity at pH 6.0, 8.5 and 10.0 without the addition of $Ca^{++}$ and at pH 10 with addition of $Ca^{++}$. The plate test described in Example 11 of WO 88/02775 (corresponding to JP-W 1-501120) was used.

|  |  | Lipase activity | | | |
|---|---|---|---|---|---|
| Species | Strain | pH 6 | pH 8.5 | pH 10 | pH 10 + $Ca^{++}$ |
| G. catenulatum | NN100802 | — | 2 | 2 | 2 |
| G. aureum | NN102987 | 1 | 1 | 1 | 1 |
| G. sagariensis | NN102989 | 1 | 2 | 2 | 2 |
| G. ammoniophilum | NN102992 | 1 | 2 | 2 | 2 |
| G. flavum | NN102995 | 2 | 3 | 2 | 2 |
| G. nigrovirens | NN102996 | 1 | 1 | 1 | 1 |
| G. solani | NN102998 | 2 | 2 | 3 | 3 |
| Gliocladium sp. | NN140631 | — | 2 | 2 | — |
| G. roseum | NN141784 | — | 2 | 2 | — |
| G. roseum | NN141961 | — | 1 | 1 | — |
| T. saccata | NN102806 | — | 2 | 2 | — |

It is seen that in this semi-quantitative test, all the above lipase preparations show nearly the same activity in the range pH 6–10, with and without calcium addition.

Example 3
Production of Lipolytic Enzyme from Gliocladium sp.

A seed culture was prepared by inoculating Gliocladium sp. CBS 173.96 from a slant of PDA (product of Difco) to one shake flask with shaking for 2 days at 27° C. A main culture was prepared by using the seed culture to inoculate 50 shake flasks with 100 ml of NOMO 16 for 5 days at 27° C. with shaking.

3,000 ml of cell-free broth with a lipase activity of 11 LU/ml was recovered after removal of the cell mass, that was directly employed for the purification.

Example 4
Purification of Lipolytic Enzyme from Gliocladium sp.

0.5% CHAPS was added to the culture broth from Example 3. This was centrifuged at 45,000 rpm for 1 hour and filtered on a 0.8 μm filter. The filtrate was applied onto a gel filtration column (Superdex, product of Pharmacia) using 50 mM Tris-HCl buffer (pH 8.5 with 0.2 M NaCl.

Example 5
Production of Lipolytic Enzyme from G. solani

A seed culture was prepared by inoculating G. solani CBS 707.86 from a slant of PDA (product of Difco) to two shake flasks with shaking for 2 days at 27° C. A main culture was prepared by using the seed culture to inoculate 50 shake flasks with 100 ml of Agar 30 for 5 days at 27° C. with shaking. 4,900 ml of cell-free broth with a lipase activity of 49 LU/ml was recovered after removal of the cell mass. This was deionized and free-dried to obtain 10.2 g of powder sample with a lipase activity of 15,700 LU/g.

Example 6
Purification of Lipolytic Enzyme from G. solani

The lipolytic enzyme was purified by 2 steps, hydrophobic interaction and gel filtration. More specifically, the purification was performed as follows.

The powder sample from Example 5 was dissolved in 3 M ammonium acetate including 0.5% 3[3-Cholamidopropyl) dimethylammonio]-1-propanesulfonate (CHAPS) and centrifuged at 18,000 rpm for 20 minutes. The supernatant was filtered with 0.2 μm filter and applied onto Butyl Toyopearl column chromatography (62×200 mm). After unbound materials were washed out by 3 M ammonium acetate and then the column was washed by 50 mM sodium carbonate buffer (pH 10.0) including 0.5% CHAPS. Lipolytic activity was eluted by $H_2O$. The eluted lipolytic enzyme was applied onto gel filtration column (26×600 mm). The applied volume was 3 ml and the eluent was 35 mM sodium carbonate buffer (pH 10.0) including 0.3% CHAPS. The flow rate was 3 ml/min. The lipolytic enzyme was eluted around 225 ml.

A molecular weight of 36 kDa was calculated from the gel filtration.

Fractions containing lipolytic activity were pooled and dialyzed/concentrated by ultra-filtration. A molecular weight of the lipolytic enzyme of 22 kD was calculated form SDS-PAGE. An iso-electric point between 8.15 and 8.45 was found by IEF-PAGE.

Example 7
Production of Lipolytic Enzyme from Verticillium sp.

Seed cultures of Verticillium sp. CBS 830.95 were produced in 500 ml shake flasks containing 150 ml medium of the following composition:
Corn steep liquor: 12 g/l
Glucose: 24 g/l
To each flask is added 0.5 ml of oil and 0.5 g of $CaCO_3$.
pH is adjusted to 5.5 before autoclavation.

The flasks were inoculated with spore suspensions from slants, using 10 ml per shake flask.

After 2 days at 26° C. at 200 rpm, the seed culture was used for inoculation of shake flasks containing 150 ml of the following medium:

| Peptone | 6 g/l |
|---|---|
| Pepticase | 4 g/l |
| Yeast extract | 3 g/l |
| Beef extract | 1.5 g/l |
| Dextrose | 1 g/l |
| Olive oil | 10 g/l | pH is adjusted to 7.3–7.4 before autoclavation
Each flask was inoculated with 4 ml seed culture. The flasks were incubated at 26° C. at 200 rpm for 4 days.

Two flasks yielded respectively 6.3 LU/ml and 7.6 LU/ml. 50 flasks resulted in 4.7 l of broth which was purified.

Example 8
Purification of lipolytic enzyme from Verticillium sp.

4 l of culture broth obtained as in Example 1 with an activity of 4.4 LU/ml was purified by the following procedure.

Decyl Agarose (50 ml): The culture broth was filtered and applied on a Decyl Agarose column previously equilibrated in 10 mM Tris/0.25 M NaCl, pH 7. Bound proteins were eluted with 50% ethanol. Yield: 75%.

Q Sepharose (25 ml): The Decyl Agarose fraction was applied on a Q Sepharose column previously equilibrated in 10 mM $H_3BO_3$/KCl, pH 10 after adjusting pH to 10. Activity was eluted from 0–0.25 M NaCl using a linear gradient. Yield: 50%.

Concentration: Desalting was carried out on G-25, followed by speed vacuum freeze drying. Yield: 60%.

Example 9
Wash Performance of Lipolytic Enzyme

Lipolytic enzyme of the invention was compared to prior-art enzymes in the following washing test:

A lipolytic enzyme according to this invention (from *G. solani* NN102998) was tested by the above AiD assay and compared to a prior-art enzyme: Lipolase® (a lipase derived from *Humicola lanuginosa*).

|  | Lipase | % hydrolysis on olive oil |
|---|---|---|
| Invention | G. solani NN102998 | 23 |
| Prior art | Lipolase | 8 |
| Blank | None | 1 |

It is seen that the wash effect of the lipase of this invention is far superior to the prior art.

Example 10
Stability of Lipolytic Enzyme in Detergent Solution

The purified lipolytic enzyme from Example 2 was incubated for 30 minutes in each of the solutions shown below. The lipase activity was measured before and after the incubation, and the stability was expressed as % residual activity. Results:

| 100 mM glycine, pH 10, 45° C. | 97% |
|---|---|
| Test detergent (see below), pH 10.2, 40° C. | 99% |

The above results demonstrate an excellent stability at alkaline pH, even in the presence of detergent.

The test detergent solution had the following composition (in g/l):

| Alkyl sulfate ($C_{14}$–$C_{16}$) | 0.300 |
|---|---|
| Alcohol ethoxylate ($C_{14}$–$C_{16}$, 6 EO) | 0.650 |
| Zeolite P | 1.750 |
| $Na_2CO_3$ | 0.145 |
| Acrylate/maleate copolymer | 0.020 |
| Carboxymethyl cellulose | 0.050 |

Example 11
Cloning and Expression of Lipolytic Enzymes

In this example, lipolytic enzymes from Gliocladium sp. CBS 173, Verticillium sp. CBS 830.95 and *T. saccata* CBS 804.70 as donor organisms were cloned and expressed, using the method for "Expression cloning in yeast" described previosuly in this specificaiton.

mRNA was isolated from the donor organism, cultivated essentially as in the main culture of a preceding example with agitation to ensure sufficient aeration. Mycelia were harvested after 3–5 days' growth, immediately frozen in liquid nitrogen and stored at −80° C. A library therefrom, consisting of approx. $9 \times 10^5$ individual clones was constructed in *E. coli* as described with a vector background of 1%. Plasmid DNA from some of the pools was transformed into yeast, and 50–100 plates containing 250–400 yeast colonies were obtained from each pool.

Lipolytic enzyme-positive colonies were identified and isolated as described above. cDNA inserts were amplified directly from the yeast colonies and characterized as described in the Materials and Methods section above. The DNA sequence of the cDNA encoding the lipolytic enzyme was determined. The DNA sequence, the corresponding amino acid sequence and the lipolytic enzyme encoding region are shown in the sequence listings identified earlier in this specification.

Total DNA was isolated from a yeast colony and plasmid DNA was rescued by transformation of *E. coli* as described above. In order to express the lipolytic enzyme in Aspergillus, the DNA was digested with appropriate restriction enzymes, size fractionated on gel, and a fragment corresponding to the lipolytic enzyme gene was purified. The gene was subsequently ligated to pHD414 and digested with appropriate restriction enzymes. The resulting plasmid from each of the three donor organisms is denoted pA2L123, pA2L114 and pC1L160, respectively.

After amplification of the DNA in *E. coli* the plasmid was transformed into *Aspergillus oryzae* as described above.

Each of the transformants were tested for lipolytic enzyme activity as described above. Some of the transformants had lipolytic enzyme activity which was significantly larger than the *Aspergillus oryzae* background. This demonstrates efficient expression of the lipolytic enzyme in *Aspergillus oryzae*.

What is claimed is:

1. An isolated lipolytic enzyme, which is:
   a) a polypeptide encoded by the DNA sequence cloned into plasmid pYES 2.0 present in *Escherichia coli* deposited as DSM 10591, DSM 10590 or DSM 11298;
   b) a polypeptide having an amino acid sequence as shown in positions 1–200 of SEQ ID NO: 3, positions 1–202 of SEQ ID NO: 6, or positions 1–201 of SEQ ID NO: 8; or
   c) a polypeptide encoded by DNA that hybridizes under conditions of hybridization in 5 times SSC, 5 times Denhardt's solution, 0.5% SDS and 100 µg/ml of denatured sonicated salmon sperm DNA at 45° C. and washing in 2 times SSC, 0.5% SDS at 55° C. with:
      i) a DNA sequence cloned into plasmid pYES 2.0 present in *Escherichia coli* deposited as DSM 10591, DSM 10590 or DSM 1 1298; or
      ii) a DNA sequence shown in positions 114–713 of SEQ ID NO: 2, positions 133–738 SEQ ID NO: 5 or positions 161–763 of SEQ ID NO: 7.

2. The lipolytic enzyme of claim 1 which is derived from a filamentous fungus.

3. The lipolytic enzyme of claim 1 which is derived from Gliocladium, Verticillium or Trichophaea.

4. The lipolytic enzyme of claim 1 which is derived from *T saccata*.

5. The lipolytic enzyme of claim 1 which is derived from *G. ammoniophilum, G. aureum, G. catenulatum, G. flavum, G. nigrovirens, G. roseum, G. sagariensis* or *G. solani*.

6. The lipolytic enzyme of claim 1 which is derived from Gliocladium sp. CBS 173.96, *G. ammoniophilum* CBS 156.70, *G. aureum* IFO 9055, *G. catenulatum* NRRL 1091, *G. flavum* CBS 155.27, *G. nigrovirens* CBS 183.30, *G. roseum* CBS 126.96, *G. roseum* CBS 127.96, *G. sagariensis* IFO 9080 or *G. solani* CBS 707.86.

7. The lipolytic enzyme of claim 1 which is derived from Verticillium sp. CBS 830.95.

8. The lipolytic enzyme of claim 1 which is in the form of an enzymatic detergent additive.

9. The lipolytic enzyme of claim 1 which is in the form of a non-dusting granulate, a stabilized liquid, a slurry or a protected enzyme.

10. The lipolytic enzyme of claim 1 wherein the lipolytic enzyme is an alkaline lipolytic enzyme which is active throughout the pH range of 8–10.

11. The lipolytic enzyme of claim 1 which is derived from a strain of Gliocladium and has a lipolytic activity at pH 10 in the absence of $Ca^{++}$ above 20% of the lipolytic activity at pH 10 in the presence of 50 mM $Ca^{++}$.

12. The lipolytic enzyme of claim 1 which is derived from a strain of Gliocladium and gives a degree of hydrolysis above 15% on cotton/olive oil swatches in the Activity-in-Detergent (AiD) assay.

13. The lipolytic enzyme of claim 1 which is derived from a strain of the genus Verticillium and retains more than 90% activity after 30 minutes incubation at pH 10.2, 40° C. in a solution of 0.300 g/l $C_{14}$–$C_{18}$ alkyl sulfate, 0.650 g/l alcohol ethoxylate ($C_{12}$–$C_{14}$, 6 EO), 1.750 zeolite P, 0.145 g/l $Na_2CO_3$, 0.020 g/l acrylate/maleate copolymer and 0.050 g/l carboxymethyl cellulose.

* * * * *